United States Patent [19]

Nargessi

[11] Patent Number: 5,770,176

[45] Date of Patent: Jun. 23, 1998

[54] ASSAYS FOR FUNCTIONAL NUCLEAR RECEPTORS

[75] Inventor: Ruhangiz Dokhi Nargessi, Alameda, Calif.

[73] Assignee: Chiron Diagnostics Corporation, East Walpole, Mass.

[21] Appl. No.: 569,977

[22] Filed: Dec. 8, 1995

[51] Int. Cl.[6] .................................................... A61K 5/00
[52] U.S. Cl. ......................... 424/1.49; 435/6; 435/91.2; 435/7.1; 435/7.9; 435/7.2; 536/23.1; 536/24.3; 536/24.33
[58] Field of Search ............................ 424/1.49; 435/6, 435/91.2, 7.1–7.9; 536/23.1, 24.3, 24.33

[56] References Cited

U.S. PATENT DOCUMENTS

| | | | |
|---|---|---|---|
| 4,215,102 | 7/1980 | Lee | 424/3 |
| 4,232,001 | 11/1980 | Jensen et al. | 424/1 |
| 4,293,536 | 10/1981 | Jensen et al. | 424/1 |
| 4,711,856 | 12/1987 | Spelsberg | 436/504 |
| 4,742,000 | 5/1988 | Greene | 435/7 |
| 5,124,246 | 6/1992 | Urdea et al. | 435/6 |
| 5,292,638 | 3/1994 | Benz et al. | 435/6 |
| 5,407,795 | 4/1995 | Kolberg et al. | 435/5 |
| 5,605,665 | 2/1997 | Clark et al. | 422/102 |

OTHER PUBLICATIONS

Abbott Laboratories, "Immunological Test System as an Aid in Assessing the Likelihood of Response to Hormonal Therapy and in the Management of Breast Cancer Patients," *Abbott ER–EIA Monoclonal* Brochure 83–5167/R5 (1989).
Abbott Laboratories, "Immunocytochemical Assay for the Detection of Human Estrogen Receptor," *Abbott ER–ICA Monoclonal* Brochure 83–5963/R8 (1990).
Abbott Laboratories, "Immunoassay for the Quantitative Measurement of Human Progesterone Receptor in Breast Tumor Tissue Cytosol," *Abbott PgR–EIA Monoclonal* Brochure 83–6024/R4 (1990).
Anolik et al., "Differential Impact of Flanking Sequences on Estradiol–vs 4–Hydroxytamoxifen–Liganded Estrogen Receptor Binding to Estrogen Responsive Element DNA," *J. Steroid Biochem. Molec. Biol.*, 46(6): 713–730 (1993).
Anolik et al., "Cooperative Binding of Estrogen Receptor to DNA Depends on Spacing of Binding Sites, Flanking Sequence, and Ligand," *Biochemistry*, 34: 2511–2520 (1995).
Baniahmad and Tsai, "Mechanisms of Transcriptional Acivation by Steroid Hormone Receptors," *Journal of Cellular Biochemistry*, 51: 151–156 (1993).
Beato, "Gene Regulation by Steroid Hormones," *Cell*, 56: 335–344 (Feb. 10, 1989).
Benz and Scott, "DNA Binding Estrogen Receptor Isoforms in Human Breast Tumors," *Clinical Research*, 38(2): 311A (1990).

(List continued on next page.)

*Primary Examiner*—W. Gary Jones
*Assistant Examiner*—Dianne Rees
*Attorney, Agent, or Firm*—Arthur S. Morgenstern; Leona L. Lauder; Robert P. Blackburn

[57] ABSTRACT

Methods and test kits for detecting, or detecting and quantitating functional nuclear receptors in cell or tissue samples are disclosed. Such methods provide highly sensitive assays requiring small sample sizes and short turnaround times. The methods are useful in developing prognoses and/or treatment programs for cancer patients, especially in determining whether therapy to interfere with the receptor's activation of gene transcription, such as, endocrine therapy, would be helpful.

64 Claims, 6 Drawing Sheets

OTHER PUBLICATIONS

Berkenstam et al., "Hormonal Regulation of Estrogen Receptor Messenger Ribonucleic Acid in T47D$_{co}$ and MCF–7 Breast Cancer Cells," *Mol. Endocrinol.*, 3(1): 22–28 (1989).

Dudley, "The Ciba Corning ACS: 180™ Automated Immunoassay System," *Journal of Clinical Immunoassay*, 14(2): 77–82 (Summer 1991).

Du Pont, RIANEN$^R$ Assay System: [$^{125}$I] Estrogen Receptor Assay Kit, Du Pont Company Catalog No.: NEA–089 Instruction Manual. Vol. No., page No. not applicable.

Fernandez et al., "Activated Oestrogen Receptors in Breast Cancer and Response to Endocrine Therapy," *Eur. J. Cancer Clin. Oncol.*, 20(1): 41–46 (1984).

Holmes et al., "Measurement of Estrogen and Progesterone Receptors in Human Breast Tumors: Enzyme Immunoassay Versus Binding Assay," *Journal of Clinical Oncology*, 8(6): 1025–1035 (Jun. 1990).

Horwitz et al., "Predicting Response to Endocrine Therapy in Human Breast Cancer: A Hypothesis," *Science*, 189: 726–727 (Aug. 1975).

Klein–Hitpass et al., "Specific Binding of Estrogen Receptor to the Estrogen Response Element," *Molecular and Cellular Biology*, 9(1): 43–49 (Jan. 1989).

Kumar and Chambon, "The Estrogen Receptor Binds Tightly to Its Responsive Element as a Ligand–Induced Homodimer," *Cell*, 55: 145–156 (Oct. 7, 1988).

Lannigan and Notides, "Estrogen receptor selectively binds the 'coding strand' of an estrogen responseive element," *PNAS* (USA) 86: 863–867 (Feb. 1989).

Lehrer et al., "Oestrogen receptor B–region polymorphism and spontaneous abortion in women with breast cancer," *The Lancet*, 335: 622–624 (Mar. 17, 1990).

Lopez de Haro et al., "Localization of an estrogen receptor binding site near the promoter of the uteroglobin gene," *FEBS Letters*, 265(1,2): 20–22 (Jun. 1990).

Ludwig, et al., "A Microtiter Well Assay for Quantitative Measurement of Estrogen Receptor Binding to Estrogen–Responsive Elements," *Mol. Endocrinol.*, 4(7): 1027–1033 (1990).

Masood, "Estrogen and Progesterone Receptors in Cytology: A Comprehensive Review," *Diagnostic Cytopathology*, 8(5): 475–491 (1992).

May et al., "A new approach allowing an early prognosis in breast cancer: the ratio of estrogen receptor (ER) ligand binding activity to the ER–specific mRNA level," *Oncogene*, 4: 1037–1042 (1989).

Murdoch et al., "Estrogen Receptor Binding to a DNA Response Element in Vitro Is Not Dependent upon Estradiol," *Biochemistry*, 29,(36): 8377–8385 (1990).

Peale et al., "Rapid Purification of the Estrogen Receptor by Seqence–Specific DNA Affinity Chromatography," *Biochemistry*, 28(22):8671–8675 (Oct. 31, 1989).

Sklarew et al., "Quantitative Imaging of Immunocytochemical (PAP) Estrogen Receptor Staining Patterns in Breast Cancer Sections," *Cytometry*, 11: 359–378 (1990).

Traish et al., "Identification of structurally altered estrogen receptors in human breast cancer by site–directed monoclonal antibodies," *Steroids*, 60: 467–474 (1995).

Wittliff, "Steroid–Hormone Receptors in Breast Cancer," *Cancer*, 53: 630–643 (1984).

Elasser et al. Biochemistry 30: 11140–11146, 1991.

Dame et al. Biochemistry 25: 4523–4535, 1986.

Foster Diss Abst 52; p. 1235, 1991.

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:

(A) LENGTH: 304 base pairs
(B) TYPE: nucleic acid
(C) STRANDEDNESS: double
(D) TOPOLOGY: linear (ii) MOLECULE TYPE:
(A) DESCRIPTION: an estrogen response element segment octamer (iii) HYPOTHETICAL: NO (iv) ANTI-SENSE: NO (xi) SEQUENCE DESCRIPTION: SEQ ID NO: 1:

```
CCAGGTCAGA GTGACCTGAG CTAAAATAAC ACATTCAGCC AGGTCAGAGT GACCTGAGCT      60
AAAATAACAC ATTCAGCCAG GTCAGAGTGA CCTGAGCTAA AATAACACAT TCAGCCAGGT     120
CAGAGTGACC TGAGCTAAAA TAACACATTC AGCCAGGTCA GAGTGACCTG AGCTAAAATA     180
ACACATTCAG CCAGGTCAGA GTGACCTGAG CTAAAATAAC ACATTCAGCC AGGTCAGAGT     240
GACCTGAGCT AAAATAACAC ATTCAGCCAG GTCAGAGTGA CCTGAGCTAA AATAACACAT     300
TCAG                                                                  304
```

(2) INFORMATION FOR SEQ ID NO: 2:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE:
(A) DESCRIPTION: a progesterone, androgen and mineralocorticoid response element segment consensus sequence; glucocorticoid response element segment consensus sequence of positively modulated genes (iii) HYPOTHETICAL: NO (iv) ANTI-SENSE: NO (x) PUBLICATION INFORMATION:
(A) AUTHORS: Beato, M.
(B) TITLE: Gene Regulation by Steroid Hormones
(C) JOURNAL: Cell
(D) VOLUME: 56
(F) PAGES: 335-344
(G) DATE: 10-Feb-1989

(xi) SEQUENCE DESCRIPTION: SEQ ID NO: 2:

```
GGTACANNNT GTTCT                                                       15
```

(2) INFORMATION FOR SEQ ID NO: 3:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE:
(A) DESCRIPTION: estrogen response element segment consensus sequence (iii) HYPOTHETICAL: NO (iv) ANTI-SENSE: NO (x) PUBLICATION INFORMATION:
(A) AUTHORS: Beato, M.
(B) TITLE: Gene Regulation by Steroid Hormones
(C) JOURNAL: Cell (D) VOLUME: 56
(F) PAGES: 335-344
(G) DATE: 10-Feb-1989

(xi) SEQUENCE DESCRIPTION: SEQ ID NO: 3:

AGGTCANNNT GACCT 15

(2) INFORMATION FOR SEQ ID NO: 4:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE:
(A) DESCRIPTION: ecdysone response element segment consensus sequence (iii) HYPOTHETICAL: NO (iv) ANTI-SENSE: NO (x) PUBLICATION INFORMATION:
(A) AUTHORS: Beato, M.
(B) TITLE: Gene Regulation by Steroid Hormones
(C) JOURNAL: Cell
(D) VOLUME: 56
(F) PAGES: 335-344
(G) DATE: 10-Feb-1989

(xi) SEQUENCE DESCRIPTION: SEQ ID NO: 4:

AGGGTTNNNT GCACT 15

(2) INFORMATION FOR SEQ ID NO: 5:

(i) SEQUENCE CHARACTERISTICS:
(A) LENGTH: 19 base pairs
(B) TYPE: nucleic acid
(C) STRANDEDNESS: double
(D) TOPOLOGY: linear (ii) MOLECULE TYPE:
(A) DESCRIPTION: thyroid hormone and retinoic acid response element segment consensus sequence (iii) HYPOTHETICAL: NO (iv) ANTI-SENSE: NO (x) PUBLICATION INFORMATION:
(A) AUTHORS: Beato, M.
(B) TITLE: Gene Regulation by Steroid Hormones
(C) JOURNAL: Cell
(D) VOLUME: 56
(F) PAGES: 335-344
(G) DATE: 10-Feb-1989

(xi) SEQUENCE DESCRIPTION: SEQ ID NO: 5:

TCAGGTCANN NTGACCTGA 19

(2) INFORMATION FOR SEQ ID NO: 6:

(i) SEQUENCE CHARACTERISTICS:
(A) LENGTH: 15 base pairs
(B) TYPE: nucleic acid
(C) STRANDEDNESS: double
(D) TOPOLOGY: linear (ii) MOLECULE TYPE:
(A) DESCRIPTION: glucocorticoid response element segment consensus sequence of repressed genes (iii) HYPOTHETICAL: NO (iv) ANTI-SENSE: NO (x) PUBLICATION INFORMATION:
(A) AUTHORS: Beato, M.
(B) TITLE: Gene Regulation by Steroid Hormones
(C) JOURNAL: Cell
(D) VOLUME: 56
(F) PAGES: 335-344
(G) DATE: 10-Feb-1989

(xi) SEQUENCE DESCRIPTION: SEQ ID NO: 6:

ATYACNNNNT GATCW 15

(2) INFORMATION FOR SEQ ID NO: 7:

(i) SEQUENCE CHARACTERISTICS:
(A) LENGTH: 38 base pairs
(B) TYPE: nucleic acid
(C) STRANDEDNESS: double
(D) TOPOLOGY: linear (ii) MOLECULE TYPE:
(A) DESCRIPTION: an estrogen response element (ERE) segment (iii) HYPOTHETICAL: NO (iv) ANTI-SENSE: NO (xi) SEQUENCE DESCRIPTION: SEQ ID NO: 7:

CCAGGTCAGA GTGACCTGAG CTAAAATAAC ACATTCAG 38

(2) INFORMATION FOR SEQ ID NO: 8:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE:
(A) DESCRIPTION: an estrogen response element (ERE) segment consensus sequence (xi) SEQUENCE DESCRIPTION: SEQ ID NO: 8:

GGTCAGAGTG ACC 13

(2) INFORMATION FOR SEQ ID NO: 9:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE:
(A) DESCRIPTION: an estrogen response element (ERE) segment consensus sequence (xi) SEQUENCE DESCRIPTION: SEQ ID NO: 9:

GGTCANNNTG ACC 13

(2) INFORMATION FOR SEQ ID NO: 10:

(i) SEQUENCE CHARACTERISTICS:
(A) LENGTH: 13 base pairs
(B) TYPE: nucleic acid
(C) STRANDEDNESS: double
(D) TOPOLOGY: linear (ii) MOLECULE TYPE:
(A) DESCRIPTION: an estrogen response element (ERE) segment ( x i ) SEQUENCE DESCRIPTION: SEQ ID NO: 10:

GGTCACAGTG ACC                                                                                                      13

( 2 ) INFORMATION FOR SEQ ID NO: 11:

( i ) SEQUENCE CHARACTERISTICS:
                ( A ) LENGTH: 18 base pairs
                ( B ) TYPE: nucleic acid
                ( C ) STRANDEDNESS: double
                ( D ) TOPOLOGY: linear ( i i ) MOLECULE TYPE:
                ( A ) DESCRIPTION: a thyroid (T3) response element segment ( x ) PUBLICATION INFORMATION:
                ( A ) AUTHORS: Locker and Buzard
                ( B ) TITLE: A dictionary of transcription control sequences
                ( C ) JOURNAL: J. DNA Sequencing and Mapping
                ( D ) VOLUME: 1
                ( F ) PAGES: 3-11
                ( G ) DATE: 1990

( x i ) SEQUENCE DESCRIPTION: SEQ ID NO: 11:

AGGTAAGATC AGGGACGT                                                                                                 18

( 2 ) INFORMATION FOR SEQ ID NO: 12:

( i ) SEQUENCE CHARACTERISTICS:
                ( A ) LENGTH: 13 base pairs
                ( B ) TYPE: nucleic acid
                ( C ) STRANDEDNESS: double
                ( D ) TOPOLOGY: linear ( i i ) MOLECULE TYPE:
                ( A ) DESCRIPTION: estrogen response element segment for human
                        oxytocin gene ( x ) PUBLICATION INFORMATION:
                ( A ) AUTHORS: Anolik et al.
                ( B ) TITLE: Differential Impact of Flanking Sequences on
                        Estradiol- VS 4-Hydroxytamoxifen-liganded Estrogen
                        Receptor Binding to Estrogen Responsive Element DNA
                ( C ) JOURNAL: J. Steroid Biochem. Molec. Biol.
                ( D ) VOLUME: 46
                ( E ) ISSUE: 6
                ( F ) PAGES: 713-730
                ( G ) DATE: 1990

( x i ) SEQUENCE DESCRIPTION: SEQ ID NO: 12:

GGTGACCTTG ACC                                                                                                      13

( 2 ) INFORMATION FOR SEQ ID NO: 13:

( i ) SEQUENCE CHARACTERISTICS:
                ( A ) LENGTH: 13 base pairs
                ( B ) TYPE: nucleic acid
                ( C ) STRANDEDNESS: double
                ( D ) TOPOLOGY: linear ( i i ) MOLECULE TYPE:
                ( A ) DESCRIPTION: estrogen response element segment for human
                        c-fos gene ( x ) PUBLICATION INFORMATION:
                ( A ) AUTHORS: Anolik et al.
                ( B ) TITLE: Differential Impact of Flanking Sequences on
                        Estradiol- VS 4-Hydroxytamoxifen-liganded Estrogen
                        Receptor Binding to Estrogen Responsive Element DNA
                ( C ) JOURNAL: J. Steroid Biochem. Molec. Biol.
                ( D ) VOLUME: 46
                ( E ) ISSUE: 6
                ( F ) PAGES: 713-730
                ( G ) DATE: 1990

(x i) SEQUENCE DESCRIPTION: SEQ ID NO: 13:

CGGCAGCGTG ACC  13

(2) INFORMATION FOR SEQ ID NO: 14:

(i) SEQUENCE CHARACTERISTICS:
    (A) LENGTH: 13 base pairs
    (B) TYPE: nucleic acid
    (C) STRANDEDNESS: double
    (D) TOPOLOGY: linear (i i) MOLECULE TYPE:
    (A) DESCRIPTION: estrogen response element segment for human
        prolactin gene (x) PUBLICATION INFORMATION:
    (A) AUTHORS: Anolik et al.
    (B) TITLE: Differential Impact of Flanking Sequences on
        Estradiol- VS 4-Hydroxytamoxifen-liganded Estrogen
        Receptor Binding to Estrogen Responsive Element DNA
    (C) JOURNAL: J. Steroid Biochem. Molec. Biol.
    (D) VOLUME: 46
    (E) ISSUE: 6
    (F) PAGES: 713-730
    (G) DATE: 1990

(x i) SEQUENCE DESCRIPTION: SEQ ID NO: 14:

TGTCACCTTG GCC  13

ASSAYS FOR FUNCTIONAL NUCLEAR RECEPTORS

FIELD OF THE INVENTION

The present invention is in the general area of the medical arts. More specifically, it relates to methods for detecting, or detecting and quantitating functional nuclear receptors. A primary use for such methods is in cancer prognosis and in making therapeutic decisions about cancer patients.

BACKGROUND OF THE INVENTION

Regulation of gene expression involves a large number of transcription factors with unique DNA-recognition properties. Many transcription factors belong to families of related proteins, the members of which bind to similar but distinct DNA sequences.

Nuclear receptors constitute a superfamily of ligand-activated transcription factors that interact with response elements within regulated genes. Nuclear receptors include receptors for steroid hormones, thyroid hormones, hormonal forms of vitamin A and D, peroxisomal activators, and ecdysone. Exemplary of steroid hormone receptors are estrogen receptor (ER) and progesterone receptor (PR).

Gene regulation by steroid hormones has been an active area of research since the discovery of puff induction by ecdysone in giant chromosomes of insects. [Clever and Karlson, *Exp. Cell Res.*, 20: 623 (1960).] Steroid hormone receptors were characterized and purified, hormonally regulated genes were cloned, and hormone response sequences were identified in the vicinity of genes regulated by steroid hormones. Dozens of regulatory elements for steroid hormones have been described, and the cDNAs for virtually all known hormone receptors have been cloned. [Evans, *Science*, 240: 889 (1988).]

It has been widely proposed that steroid hormones mediate their biological responses by crossing the plasma membranes of cells and interacting with receptor proteins, that is, steroid hormone receptors, in the cytosol or nucleus, to form complexes. The ligand/receptor complexes then accumulate in the nucleus of cells where they bind to specific regulatory DNA sequences, i.e., hormone response elements (HREs). A dimer of the steroid hormone receptor/ligand complex is considered to bind to the appropriate response element, specifically to the core sequence of the response element, and by so binding, the steroid hormone receptor/ligand complex affects the transcription rate of dependent gene(s). The complexes may also affect the stability of specific mRNAs. HREs have been identified and characterized by several methods and have been shown to contain consensus sequences for the hormonal receptors. [Beato, M., *Cell*, 56: 335–344 (1989); Lopez de Haro et al., *FEBS Lett.*, 265: 20–22 (1990); Baniahmad and Tsai, *J. Cell Biochem*, 51: 151–156 (1993).]

During the past few decades, endocrine therapy has been found to be effective in a percentage of cancer patients, notably those with breast, uterine or prostate cancer. Endocrine therapy may palliate symptoms or delay the advance of the cancer. [E.g., Beatson, G. T., *Lancet*, 2: 104 (1986).] For example, it has been observed that certain human breast cancer tissues are steroid hormone dependent, that is, deprivation of the supportive hormones result in regression of tissue growth and cell proliferation. Typically, endocrine therapy involves the administration of androgen or anti-estrogens, such as, estrogen analogs, and/or surgical ablation, such as, bilateral adrenalectomy, hypophysectomy, or ovariectomy.

The value of estrogen (ER) and progesterone receptor (PR) measurements in predicting breast cancer patients response to endocrine therapy and overall survival has become well established. [Wittliff, J. L., *Cancer.* 53: 630–643 (1984); Masood, S., *Diagnostic Cytopathology*, 8: 475–491 (1991)]. ER and PR are found in the cell cytoplasm and nucleus of target tissue, such as, uterine, ovarian and mammary gland tissues. The presence or absence of ER and PR in primary or metastatic tumor tissue is presently used to predict whether a patient is expected to respond to endocrine therapy, and therefore, whether to select endocrine therapy over cytotoxic chemotherapy or radiation. For example, the presence of ER is correlated with expected responsivity of the cancer to endocrine therapy; whereas the absence of ER is correlated with nonresponsivity of the cancer to endocrine therapy. Thus, the identification of the steroid hormone receptors, ER and PR, is considered to have clinical utility in the prognosis of certain cancers notably, breast, ovarian and uterine cancers, and in determining whether endocrine therapy would be a useful treatment modality.

However, despite the established clinical utility of ER measurement in identifying breast cancer patients who respond to some type of endocrine therapy, only about 55% to 60% of ER-positive breast cancer patients respond to endocrine therapy. [Fernandez et al., *Eur. J. Clin. Oncol.*, 20(1): 41 (1984).] It is the thesis of the instant invention that the cancerous tissues of ER-positive breast cancer patients who do not respond to endocrine therapy contain nonfunctional ERs, that is, ERs that do not effectively bind to estrogen response elements (EREs).

Currently ER and/or PR values in human tumor specimens are determined in general by either ligand binding assays or immunochemical techniques, which provide no information on the structural or functional integrity of ER. Such assays do not identify functional ER and/or PR but only the presence of ER or PR that bind to their respective ligands or those that have an antigenic site recognized by an anti-PR or anti-ER antibody.

Further, the standard biochemical ligand binding assays (LBAs) for determination of ER and PR levels [Du Pont ER Assay Kit (assay to measure estrogen receptor (ER) binding capacity in breast tumor tissue cytosol using $^{125}I$ labeled estrogen); Du Pont PR Assay Kit] have major drawbacks. Such drawbacks include lability of the receptor binding sites, need for a large sample size, lengthy and laborious assay procedures, handling hazardous radioactive reagents and interference from endogenous steroids. [Holmes et al., *J. Clin. Oncol.*, 8: 1025 (1990); King et al., *Cancer Res..* 45: 293–304 (1985); Thorpe, S. M., *Cancer Res.*, 47: 6572–6575 (1987)]. A LBA only recognizes the receptor population capable of binding to the receptor-specific ligand.

The production of antibodies against ER and PR [Greene et al., *PNAS* (USA) 74: 3681–3685 (1977); Greene et al., *Biochemistry*, 77: 5115–5119 (1980); Press and Greene, *Endocrinol*, 122: 1165–1175 (1988); Traish et al., *Endocrinol*, 125: 172–179 (1989); and Traish and Wotiz, *Endocrinol*, 127: 1167–1175 (1990)] led to the development of receptor assays which circumvent some of the LBA limitations. Such assays recognize antigenic determinants rather than receptor binding sites; and such assays require smaller sample size, do not involve radioactive reagents,and are not affected by endogenous steroids.

Such receptor assays based on antibodies have been developed by a number of investigators [Tamura et al., *Eur. J. Cancer Clin. Oncol.*, 20: 1261–1277 (1984); King and Weigand, *Pathologist:* 15–19 (1986)], and commercial assays have been introduced by Abbott Laboratories [Abbott Park, Ill. (USA)] during the last decade. Those assays are either based on a conventional sandwich enzyme immunoassay (EIA) using tissue cytosols [Abbott ER-EIA Monoclonal Kit (an immunoassay to measure ER in tissue cytosols from breast cancer patients); Abbott PgR-EIA Monoclonal (an immunoassay to measure PR in breast tumor tissue cytosols)], or involve an immunohistochemistry (IHC)/immunocytochemistry (ICA) procedure using fresh/frozen tissue sections. [Abbott ER-ICA Monoclonal Kit (an immunocytochemical assay for the detection of estrogen receptors in human breast tissue).] Those antibody-based assays do not discriminate between ligand-occupied and non-occupied receptors and reflect the total content of receptors, nonfunctional and functional. Although such assays have attractive features, they have not successfully replaced the standard LBAs, mainly due to the lack of correlation of their results with LBA results and to the expensive cost of the reagents.

A significant number of false positive and false negative results found by current methodologies for ER and PR call for more effective tests. False positive results are herein considered to be those wherein nonfunctional receptors are detected, that is, receptors that do not bind to their response elements. In that case where a tumor contains nonfunctional receptors, endocrine therapy would be useless. Precious time is therefore wasted upon useless endocrine therapy while the cancer advances, whereas more aggressive treatments, such as, chemotherapy or radiation, may have halted the cancer's progression. False negative results are herein considered to be those wherein functional receptors are not detected. In such cases, the opportunity for endocrine therapy, which may have resulted in tumor regression, is missed; and the patient is subjected probably unneccessarily to more toxic therapies.

The instant invention provides more effective tests in that the assays disclosed determine whether nuclear receptors present in cancerous tissues are functional or not, that is, whether they bind or not to their response elements. Whereas neither the LBAs nor the conventional immunoassays serve to identify the subpopulation of ER-positive breast cancer patients that are resistant to endocrine therapy and require cytotoxic chemotherapy or radiation, the instant invention does identify that sub-population, in that the assays described herein identify functional receptors and not nonfunctional receptors.

Others have found that the predictability of responsiveness to endocrine therapy improves when two or three parameters are used simultaneously. Horowitz et al., *Science,* 1989: 726 (29 Aug., 1975) hypothesized that ER-positive breast cancer patients that are resistant to endocrine therapy could be identified by the absence of PR. Fernandez et al., supra; King et al., "The measurement of receptors for oestradiol and progesterone in human breast tumours, IN: *Steroid Receptor Assays in Human Breast Tumours: Methodological and Clinical Aspects*, pp. 55–72 (King, R. J. B. ed.) (Alpha Omega Alpha; Cardiff 1979); and Leake et al., *Br. J. Cancer,* 43: 59 (1981) agreed with that hypothesis, and also determined that the simultaneous detection of nuclear and cytosol ER improves predictability made by the presence of cytosol ER alone. Fernandez et al., supra, also reported that tumors which have cytoplasmic ER that are able to bind to oligo (dT)-cellulose are more likely to respond to endocrine therapy than are tumors that have cytoplasmic ER that are not able to so bind.

Benz and Scott, U.S. Pat. No. 5,292,638 (issued Mar. 8, 1994), entitled "Method of Determining Functional Estrogen Receptors for Prognosis of Cancer" discloses modifications of a gel retardation (band shift) assay to detect estrogen response elements (EREs) complexed to ER, originally described in Klein-Hitpass et al., *Mol. Cell. Biology,* 9 (1): 43 (January 1989). Complex methods are claimed in Benz and Scott for determining the relative proportion of functional estrogen receptor in human tumor tissue.

The assays of the instant invention provide relatively simple, quick and highly sensitive methods of detecting, or detecting and quantitating functional nuclear receptors, including steroid hormone receptors, such as, ER and PR, which are capable of binding to their respective DNA response elements. The assays of this invention therefore can aid in effectively predicting patient response to endocrine therapy, and in determining the prognosis and treatment for cancer patients.

SUMMARY OF THE INVENTION

In one aspect, the methods of the instant invention in detecting functional nuclear receptors are based on the simultaneous binding of a nuclear receptor/ligand complex to a response element segment and to an antibody, which antibody specifically binds to the nuclear receptor under assay when it is bound both to its ligand and to its associated DNA response element. Methods are disclosed for detecting the presence or absence of functional nuclear receptors in a cell or tissue sample, or of detecting and quantitating functional nuclear receptors in a cell or tissue sample comprising:

(a) contacting said sample with the following: (1) ligand to which the nuclear receptor under assay binds; (2) antibody that is capable of specifically binding to the nuclear receptor under assay when said receptor is bound both to its associated ligand and response element; and (3) a nucleic acid reagent containing one or more response element segments to which the nuclear receptor under assay binds; wherein the sample may be contacted with the ligand, the nucleic acid reagent and the antibody components simultaneously, with two of said components simultaneously, or sequentially with said three components in any order; and (b) correlating the specific binding of said nucleic acid reagent, said ligand and said antibody to a substance in said sample with the presence of functional nuclear receptors in said sample, or correlating the amount of complexes formed by the specific binding of said nucleic acid reagent, said ligand, said antibody and a substance in said sample with the amount of functional nuclear receptors in said sample.

Another aspect of this invention concerns methods wherein a ligand is not required for activation of the receptor, for example, wherein high temperature (for example, 37° C.), high salt content (for example, 0.4M KCl) and/or adenosine triphosphate (ATP) is used to activate the receptor instead of the receptor's ligand.

The nucleic acid reagents used in such methods can be isolated from naturally occurring sources or can be prepared recombinantly or synthetically; preferably they are prepared synthetically. Preferably they comprise one to 15 response element segments, more preferably, one to 10 response element segments, still more preferably, one to eight response element segments, and even more preferably four to eight response element segments. It is preferred that when there is more than one response element segment in a nucleic acid reagent, that the core sequences of said response elements be the same; whereas the spacer sequences and flanking sequences may vary. Preferably the flanking sequences are naturally occurring sequences that are AT-rich. Still more preferably, when there are more than one response element segment in the nucleic acid reagents of this invention, those response elements are copies of each other, for example, dimers, trimers, tetramers, pentamers, hexamers, septamers, octamers, etc., still more preferably tandem repeats.

Such methods have the advantage of being able to be carried out in an automated immunoassay system, such as, the ACS:180TM Automated Chemiluminescence System [CCD; Medfield, Mass. (USA)]. Many different labels can be used in the methods of this invention. Chemiluminescent labels are a preferred detectable marker whether directly, as for example, by the use of an acridinium ester, or indirectly, for example, as the product of an enzymatic reaction.

A preferred embodiment for performing the methods of this invention include those wherein the antibody is attached to a solid phase, and the nucleic acid reagent is directly or indirectly linked to a detectable marker [FIG. 1]. Another preferred embodiment is that wherein the nucleic acid reagent is attached to a solid phase, and wherein the antibody is directly or indirectly linked to a detectable marker [FIG. 2]. More preferred is the former embodiment wherein the antibody is attached to the solid phase. When the nucleic acid reagent is attached to the solid phase, efforts are required to prevent non-specific binding of proteins, other than the nuclear receptor under assay, in the sample to the immobilized nucleic acid reagent. Such efforts include employing an excess of the nucleic acid reagent and including appropriate unlabeled, non-specific nucleic acids.

In the preferred embodiment wherein the antibody is attached to the solid phase, preferably the antibody and ligand are incubated with the sample, and thereafter uncomplexed sample components are removed, before the nucleic acid reagent is added.

A further preferred aspect of this invention involves the use of binding pairs. For example, in the preferred embodiment wherein the nucleic acid reagent is the tracer agent, it may be preferred for it to be conjugated to a member of a binding pair, and the detectable marker be conjugated to the other member of the binding pair. The nucleic acid reagent can then be incubated with the solid phase complex, and thereafter, uncomplexed reagents are removed, before the conjugated detectable marker is added and then detected, or detected and quantitated. A preferred binding pair is biotin and either avidin or streptavidin, more preferably biotin and streptavidin. Still more preferably, the nucleic acid reagent is biotinylated, and the avidin or streptavidin is conjugated to alkaline phosphatase or horseradish peroxidase. Still more preferably, the nucleic acid reagent is biotinylated either randomly or selectively at multiple sites, more preferably selectively at the 5' phosphorylated ends and/or at multiple sites that are not within a reponse element core sequence. A preferred means of biotinylating the nucleic acid reagent is during its synthesis.

The cell or tissue samples assayed by the methods of this invention are preferably cell or tissue extracts or cell lysates, more preferably cytosols and/or nuclear extracts. The samples are preferably vertebrate, more preferably mammalian, and still more preferably human. The sample may be prepared from biopsied tissue or from a cell suspension taken from a cancer patient, for example, a breast cancer patient. In such a case, it is usually a steroid hormone receptor, such as, ER, PR or AR, that is under assay. To minimize the invasiveness of the procedure to acquire such biopsied tissue or cell suspension from a cancer patient, it is preferred that the sample be prepared from a fine needle aspirate or from a stereotactic needle biopsy. Tissue and cell samples are taken from patients who have cancer, such as, breast, endometrial, uterine, cervical, ovarian, prostrate, vaginal or vulval cancers.

One aspect of the invention is to provide highly sensitive assays that require a minimal amount of sample for assay. That sensitivity is achieved by several factors including the use of a signal amplification system. One preferred signal amplification system comprises using a nucleic acid reagent that is biotinylated at multiple sites. After uncomplexed components are removed, streptavidin or avidin conjugated to a label, such as, HRP or AP, is added, and thereafter uncomplexed components are removed. When the label is an enzyme, an appropriate substrate, preferably a chemoluminescent substrate, is then added, and the signal is detected, or detected and quantitated.

Another preferred signal amplification system comprises the use of nucleic acid multimers that each comprise (i) an oligonucleotide unit that is complementary to a segment of the nucleic acid reagent, and (ii) a multiplicity of second oligonucleotide units that are complementary to an oligonucleotide that is labeled directly or indirectly.

Another aspect of the invention involves methods of developing a prognosis and/or a treatment program for a cancer patient. A still further aspect of the invention concerns test kits for performing the methods of this invention which comprise:

(a) an antibody that is capable of specifically binding to the nuclear receptor under assay when said receptor is bound both to its associated ligand and response element;

(b) ligand to the nuclear receptor under assay; and (c) a nucleic acid reagent containing one or more response element segments to which the nuclear receptor under assay binds.

DETAILED DESCRIPTION

Abbreviations

Figure 1:
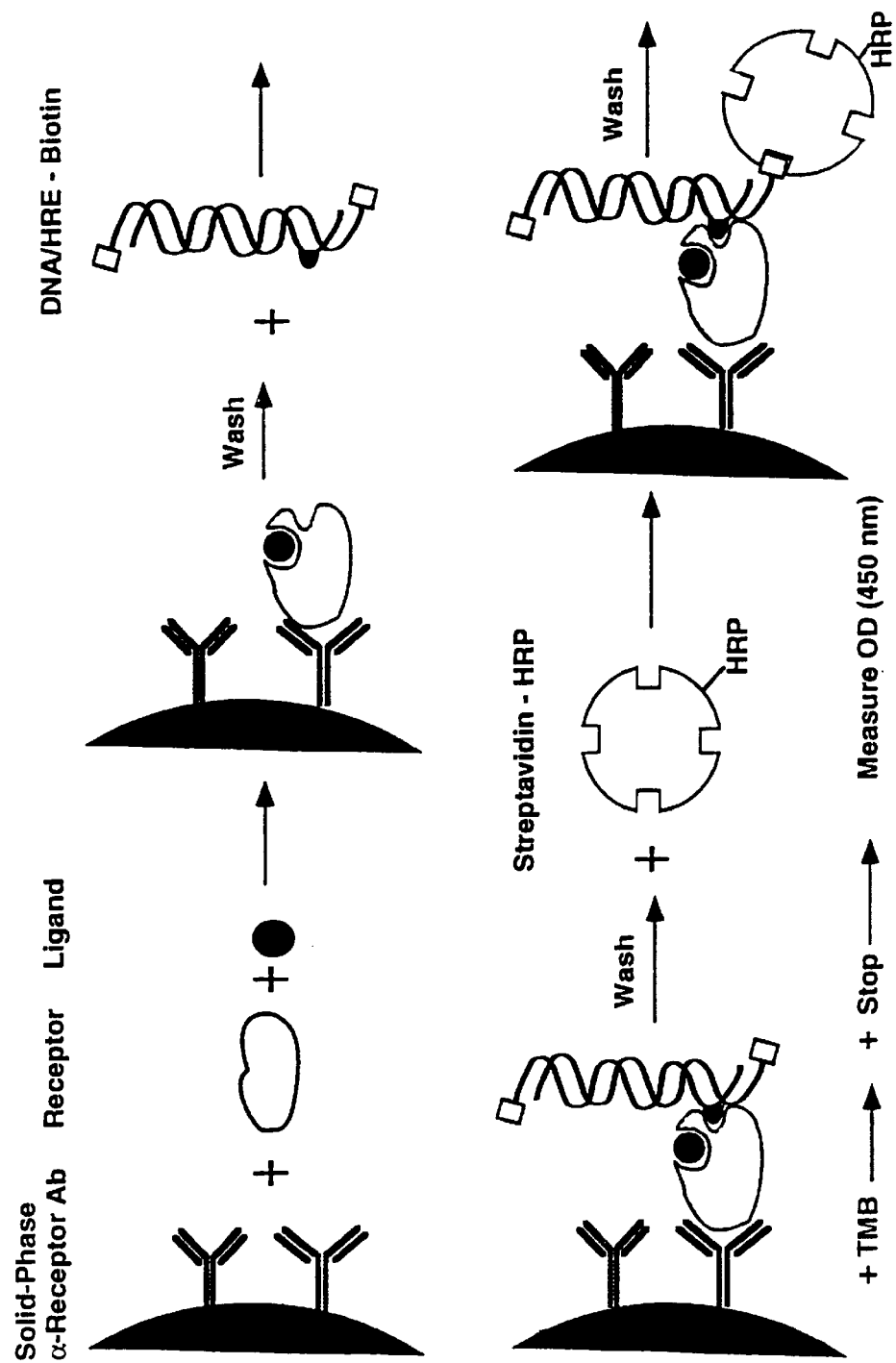
FIG. 1 provides a schematic of a preferred immunoassay embodiment of this invention to detect and quantitate functional nuclear receptors, wherein an anti-receptor antibody is used as the capture reagent. The tracer reagent in the portrayed embodiment is DNA containing a hormone responsive element (HRE) that is specific for the receptor under assay.

The following abbreviations are used herein:

| | |
|---|---|
| aa | amino acid |
| Ab | antibody |
| AE | acridinium ester |
| AH-BNHS | amino hexanoyl-biotin-N-hydroxy succinimide ester |
| AR | androgen receptor |
| ARE | androgen response element |
| ATP | adenosine triphosphate |
| BL | bioluminescent |
| bp | base pair |
| BSA | bovine serum albumin |
| CCD | Ciba Corning Diagnostics Corp. |
| CDR | complementarity determining region |
| CL | chemiluminescent |
| DSL | Diagnostic Systems Laboratories |
| Dupt | Du Pont |
| EDTA | ethylenediamine tetraacetic acid |
| EIA | enzyme immunoassay |
| ELISA | enzyme linked immunosorbent assay |
| EcRE | ecdysone response element |
| ER | estrogen receptor |
| ERE | estrogen response element |
| fmole | femtomole |
| GR | glucocorticoid receptor |
| GRE | glucocorticoid response element |
| hr | hour |
| HRE | hormone response element |
| HRP | horseradish peroxidase |
| ICA | immunocytochemistry |
| IHC | immunohistochemistry |
| LBA | ligand binding assay |
| LTR | long terminal repeat |
| M | mole |
| MAb | monoclonal antibody |
| MR | mineralocorticoid receptor |
| MRE | mineralocorticoid response element |
| min | minute |
| ml | milliliter |
| mM | millimole |
| MP | magnetizable particle |
| NADPH | reduced form of nicotinamide-adenine dinucleotide phosphate |
| ng | nanogram |
| nm | nanometer |
| nmol | nanomole |
| nt | nucleotide |
| OD | optical density |
| PBS | phosphate-buffered saline |
| PEG | polyethylene glycol |
| pNPP | paranitrophenyl phosphate |
| PR | progesterone receptor |
| PRE | progesterone response element |
| RR | retinoic acid receptor |
| RRE | retinoic acid response element |
| SDS-PAGE | sodium dodecyl sulfate-polyacrylamide gel electrophoresis |
| T3 | triiodothyronine |
| TE | 10 mM Tris-HCl, pH 7.5, 0.5 mM Na-EDTA |
| TMB | tetramethyl benzidine |
| TR | thyroid hormone receptor |
| TRAP | T3 receptor auxiliary proteins(s) |
| TRE | thyroid hormone responsive element |
| TRIS | tris(hydroxymethyl)aminomethane or amino-2-hydroxymethyl-1,3-propanediol |
| U | uterus |
| µl | microliter |
| +ve | positive |
| −ve | negative |
| × | times |

Nucleotide Symbols

The following symbols are used to represent nucleotides herein:

| Base Symbol | Meaning |
|---|---|
| A | adenine |
| C | cytosine |
| G | guanine |
| T | thymine |
| U | uracil |
| I | inosine |
| M | A or C |
| R | A or G |
| W | A or T/U |
| S | C or G |
| Y | C or T/U |
| K | G or T/U |
| V | A or C or G |
| H | A or C or T/U |
| D | A or G or T/U |
| B | C or G or T/U |
| N/X | A or C or G or T/U |

Definitions

The term "nuclear receptors" is herein defined as proteins that are ligand-activated transcriptional factors that interact with response elements within regulated genes. Nuclear receptors include receptors for steroid hormones, thyroid hormones, retinoids, hormonal forms of vitamin A and D, peroxisomal activators, and ecdysone.

The term "steroid/thyroid hormone receptors" are defined herein as nuclear receptors which affect gene activity in a hormone-dependent manner, and include receptors for steroid hormones, hormonal forms of vitamin A and D, thyroid hormones and retinoids, such as, retinoic acid.

The term "steroid hormone receptors" are defined herein as nuclear receptors that are phosphoproteins that include receptors for estrogens, progestins, androgens, glucocorticoids, mineralocorticoids and 1,25-dihydroxyvitamin D3.

The term "functional" used in conjunction with the term "receptor" herein whether nuclear receptor, steroid/thyroid hormone receptor or steroid hormone receptor, means that the so modified "receptor" is capable of binding to its respective DNA response element.

"Response element" is herein defined to mean a DNA sequence within a gene to which a nuclear receptor/ligand complex binds and thereby affects the transcription of the gene. Response elements are typically 5' to the promoters of regulated genes, but may also be downstream.

"Response element segment" is herein defined to mean a segment of a response element that contains at least the core sequence of the response element, and spacer nucleotides (nts) between the inverted repeats of the core sequence, and typically either one or two flanking sequences thereto.

A "response element core sequence" is considered herein to mean the part of a response element to which a nuclear receptor dimer complex actually physically binds, and is generally considered to consist of two inverted repeats or palindromic sequences. The two inverted repeats are separated by spacer nucleotides. For example, the core consensus sequence for ERE is herein considered to be two inverted repeats separated by 3 spacer nts as shown in SEQ. ID. NO.: 9, that is, <u>GGTCA</u>NNN<u>TGACC</u>. The underlined portions of SEQ. ID. NO.: 9 are the core sequence to which the ER/ligand (estradiol) complex dimer is believed to bind, and are seen to be palindromic when the oligomer is envisioned as double-stranded; the NNN central portion provides a spacer between the inverted repeats. Other exemplary ERE core sequences are shown in Table 1 below as the inverted repeats of SEQ. ID. NOS.: 8–10 and 12–14.

As used herein the term "complementary" intends a degree of complementarity sufficient to provide a stable duplex structure. It is understood by those in the art that nucleic acid sequences need not have perfect complementarity to provide homoduplexes. In many hybridization situations, heteroduplexes will suffice where fewer than about 10% of the bases are mismatched, ignoring loops of five or more nucleotides.

The term "antibodies" is defined herein to include not only whole antibodies but also biologically active fragments of antibodies, preferably fragments containing the antigen binding regions. Such antibodies may be prepared by conventional methodology and/or by genetic engineering. Antibody fragments may be genetically engineered, preferably from the variable regions of the light and/or heavy chains (VH and VL), including the hypervariable regions, and still more preferably from both the VH and VL regions. For example, the term "antibodies" as used herein comprehends polyclonal and monoclonal antibodies and biologically active fragments thereof including among other possibilities "univalent" antibodies [Glennie et al., *Nature,* 295: 712 (1982)]; Fab proteins including Fab' and F(ab')2 fragments whether covalently or non-covalently aggregated; light or heavy chains alone, preferably variable heavy and light chain regions (VH and VL regions), and more preferably including the hypervariable regions [otherwise known as the complementarity determining regions (CDRs) of said VH and VL regions]; Fc proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques and also by oligonucleotide-directed mutagenesis techniques [Dalbadie-McFarland et al., *PNAS* (USA), 79: 6409 (1982)].

In general, the term "steroid" is considered as "a group name for lipids that contain a hydrogenated cyclopentanoperhydrophenanthrene ring system. Some of the substances included in this group are progesterone, adrenocortical hormones, the gonadal hormones [such as, estrogen and testosterone], cardiac aglycones, bile acids, sterols (such as cholesterol), toad poisons, saponins, and some of the carcinogenic hydrocarbons." [Dorland's Illustrated Medical Dictionary, 27th Edition (W. B. Saunders Co.; Philadelphia., Pa.; 1988).]

Representative Embodiments

Described herein are novel methods for detecting, or detecting and quantitating functional nuclear receptors. In one aspect of the invention, a method is based on the simultaneous binding of the nuclear receptor under assay occupied by its ligand, to both its associated response element and to an anti-receptor antibody. An important aspect of such an embodiment requires that the anti-receptor antibody is selected such that it is known to be capable of binding to the nuclear receptor under assay when it is not only occupied by its ligand, but also when the ligand-occupied receptor is bound to its associated response element. A preferred screening process employs a gel supershift assay as described below. For other embodiments wherein the receptor is activated by other than a ligand, for example, by high temperature, high salt content, and/or ATP, the anti-receptor antibody would be screened to bind to the receptor in the appropriate activated conformation without being ligand-occupied.

Figure 2:
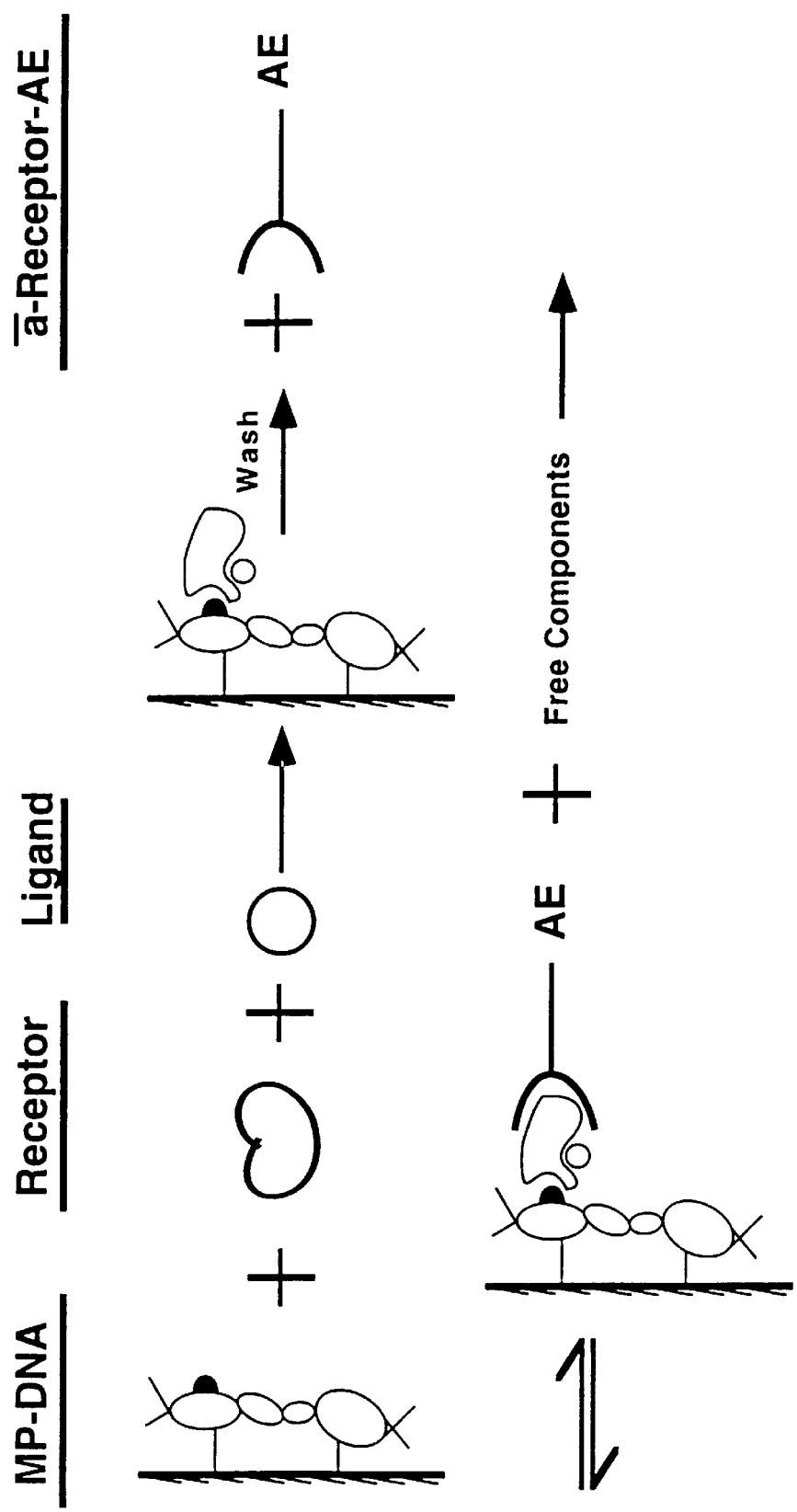
FIG. 2 provides a schematic of a preferred immunoassay embodiment of this invention to detect and quantitate functional nuclear receptors wherein DNA containing the hormone responsive element specific for the nuclear receptor under analysis, is used as the capture reagent. An anti-receptor antibody labeled with an acridinium ester (AE) is the tracer reagent.

Representative preferred embodiments of the methods of this invention are illustrated schematically in FIGS. 1 and 2 wherein the embodiment portrayed in FIG. 1, that is, wherein the anti-receptor antibody is attached to the solid phase, is particularly preferred. In FIG. 1, one form of detection scheme wherein the nucleic acid reagent is linked indirectly to a detectable marker through a binding pair (biotin/streptavidin) is used. Other preferred detection/quantitation means are detailed below. Similarly, other detection/quantitation means can be used in embodiments according to this invention wherein it is the nucleic acid reagent attached to the solid phase as in FIG. 2.

In a representative embodiment of methods according to this invention of detecting/quantitating functional nuclear receptors, wherein the receptor under assay is activated by its ligand and wherein the anti-receptor antibody is attached to the solid phase, a cytosolic preparation of a tissue sample is reacted in the presence of the specific ligand to the nuclear receptor under assay, with a monoclonal antibody specific for the ligand-occupied nuclear receptor (activated receptor) bound to its associated response element. The monoclonal antibody is immobilized on a solid phase, in this example, on a magnetizable particle (MP) or onto microtiter wells. The activated nuclear receptors are then captured by the solid phase, to which the anti-receptor antibody has been attached. After uncomplexed components are removed, for example, in a wash step, the biotinylated nucleic acid reagent containing one or more response element segments is added. The immobilized complex is then washed to remove unbound nucleic acid reagent, and streptavidin linked to HRP is then added. Uncomplexed components are again removed, preferably in a wash step, and substrate for HRP is added, which in FIG. 1 is TMB. A stop reagent is then added, and the enzymatic product is then detected or detected and quantitated, for example by optical density (OD) at 450 nm. The values obtained are proportional to the concentration of the receptor in the sample.

In the embodiment exemplified by FIG. 2, nuclear receptors in a cytosolic preparation of a tissue sample are again first reacted with the specific ligand to the nuclear receptor under assay. The ligand-occupied receptors (activated receptors) are then captured by magnetizable particles (MP) to which the nucleic acid reagent containing one or more response element segments has been coupled. The complex is washed to remove unbound materials. Antireceptor antibody conjugated with the chemiluminescent tag, acridinium ester (AE), is then added. The immobilized complex is washed to remove unbound receptors. The bound fraction is then incubated with the light reagent and the amount of light photons generated is determined in a luminometer, for example, the Ciba Corning ACS-180TM Automated Chemiluminescent System [Ciba Corning Diagnostics Corp. (CCD) E. Walpole, Mass. (USA)]. The values obtained are directly proportional to the concentration of the receptor in a sample.

The embodiments outlined above and graphically in FIGS. 1 and 2 are representative of a wide number of assay methods according to this invention. For example, the components of FIGS. 1 and 2 can be reversed; that is, the nucleic acid reagent can be attached to microtiter plates and a biotinylated anti-receptor antibody could be used analogously to the FIG. 1 format. Alternatively, anti-receptor antibody could be attached to magnetizable particles, and an AE-labeled nucleic acid reagent could be used analogously to the FIG. 2 format. Those embodiments are just a few of the many variations of the methods of this invention within the skill of one in the art.

Variations of the representative embodiments of the methods of this invention within conventional knowledge of those of skill in the art are considered to be within the scope of the instant invention. Preferred variations and more detailed embodiments are identified in the following sections.

When embodiments of the methods of this invention are used wherein the nucleic acid reagent is attached to the solid phase, it is important to take steps to avoid non-specific binding of proteins, other than the nuclear receptor under assay, within the sample to the nucleic acid reagent. For example, stringent assay conditions can be used to eliminate such non-specific binding. Also, such non-specific binding to the nucleic acid reagent can be prevented by incubating the sample with unlabelled non-specific nucleic acids, preferably non-specific DNA such as poly[d(I-dC)] in excess, or with an unlabelled appropriate non-specific single-stranded oligomer mix. Ones of skill in the art are aware of methods of optimizing by routine experimentation the assay conditions to improve the stringency of the binding conditions between the nuclear receptor under assay and its response element.

Example 1 provides representative conditions for performing the methods of this invention. Such exemplary conditions can also be used in methods wherein ligand is not used to activate the receptor, but instead high temperature, high salt content and/or ATP are used. For example, in the ELISA described in Example 1, a temperature of 37° C. may be used to activate the receptor.

Prognosis and Treatment

Methods of this invention can be used to develop a prognosis and/or a treatment program for a cancer patient. For example, such methods comprise performing a method of this invention to detect, or detect and quantitate functional nuclear receptors in a sample prepared from biopsied tissue or from a cell suspension taken from a cancer patient. The results from that method indicate whether functional nuclear receptors are present or absent in the sample, and if functional nuclear receptors are present, the quantity thereof in the sample. Based on those results, a prognosis for the patient can be made, and/or a decision on whether endocrine therapy would be useful in a treatment program for said patient can be made.

In identifying functional nuclear receptors, the methods of this invention have prognostic value, in that, they reveal a state of differentiation in pre-neoplastic/neoplastic cells or tissues that is identified with less advanced disease progression, and signal an opportunity to treat a cancer patient successfully with therapies alternative to chemotherapy and/or radiation. For example, if a patient has cancer, the presence of functional nuclear receptors indicates in general a positive prognosis, and that endocrine therapy would be helpful in treating the patient. The assay results are preferably used in conjunction with other clinical and laboratory data to assist clinicians in making individualized patient management decisions.

The methods of this invention, as indicated above, in identifying whether a patient's preneoplastic/neoplastic tissues contain functional receptors or contain nonfunctional receptors, provide important information in making therapeutic decisions concerning that patient. If a patient has pre-neoplastic/neoplastic tissues containing functional receptors, treatment designed to interfere with the receptor's activation of gene transcription could be appropriate. If a patient has pre-neoplastic/neoplastic tissues containing non-functional receptors, more aggressive therapy, such as, cytotoxic chemotherapy or radiation, could be appropriate.

Such methods are especially useful in relation to assays according to this invention wherein functional steroid hormone receptors are under assay, and wherein the patient has breast, endometrial, uterine, cervical, ovarian, prostate, vaginal or vulval cancers. More preferred are such assays wherein functional ER and PR are under assay, and wherein the patient has breast, endometrial, uterine, cervical or ovarian cancer. In the case of a patient with prostate cancer, preferred would be an assay for functional androgen receptor (AR).

The methods of this invention represent an important medical advance in that cancer patients who have tumors, wherein the nuclear receptors are nonfunctional, do not have to endure unnecessary, useless and potentially harmful surgical ablations, such as, an ovariectomy, hypophysectomy or bilateral adrenalectomy, or the administration of androgens or anti-estrogens, such as tamoxifen, megace, aminoglutethimide, and idoxifen. Further, more aggressive therapies, such as, chemotherapy and radiation, are not delayed while endocrine therapy, that can not be useful through the route of preventing nonfunctional receptors from binding to their respective response elements, is undergone.

The methods are also important for patients who have functional receptors. False negative results of previous methods had meant that patients who had functional receptors underwent toxic therapies probably unnecessarily, since endocrine therapy may have been sufficient to cause remission.

Automated Immunoassay System

The methods of this invention can be readily adapted to automated immunochemistry analyzers. To facilitate automation of the methods of this invention and to reduce the turnaround time, the anti-receptor antibody or the nucleic acid reagent, preferably the antibody, may be coupled to magnetizable particles.

A preferred automated/immunoassay system is the Ciba Corning ACS:180TM Automated Chemiluminescence System [CCD; Medfield, Mass. (USA)]. The Ciba Corning ACS:180TM Automated Immunoassay System is described in Dudley, B. S., *J. Clin. Immunoassay*, 14(2): 77 (Summer 1991). The system uses chemiluminescent labels as tracers and paramagnetic particles as solid-phase reagents. The ACS:180 system accommodates both competitive binding and sandwich-type assays, wherein each of the steps are automated. The ACS:180 uses micron-sized paramagnetic particles that maximize the available surface area, and provide a means of rapid magnetic separation of bound tracer from unbound tracer without centrifugation. Reagents can be added simultaneously or sequentially. Other tags, such as an enzymatic tag, can be used in place of a chemiluminescent label, such as, acridinium ester.

Nuclear Receptors

Representative assays to detect, or detect and quantitate functional ER in breast cancer cells are detailed herein. Ones of skill in the art understand that analogous assays to detect, or detect and quantitate other functional nuclear receptors, whose responsive elements have been identified, in various normal or preneoplastic/neoplastic tissues, such as, breast, endometrial, uterine, ovarian and prostatic tissues, can be made. For such analogous assays, appropriate antibodies that are capable of binding specifically to the nuclear receptor under assay, when it is in its activated conformation, for example, when it is bound to its ligand, and when it is bound to its DNA response element, are used. Also used are nucleic acid reagents containing one or more response element segments to which the nuclear receptor under assay binds. Exemplary antibodies and response element segments are set forth below.

Preferred analytes of the instant invention are steroid/thyroid hormone receptors; more preferred are steroid hormone receptors; still more preferred are ER and PR; and most preferred is ER. To exert their diverse effects on reproduction, development and differentiation, the steroid/thyroid hormone receptors link extracellular signals directly to transcriptional regulation. In vivo, the hormone response is mediated by binding of the ligand to its receptor, followed by the binding of the receptor-ligand complex to a specific regulatory sequence referred to as response elements of the target genes. [Baniahmad and Tsai, *J. Cell Biol.*, 51: 151 (1993).]

Molecular cloning and structure/function analyses have revealed that all members of the steroid/thyroid hormone/retinoic acid receptor family have a similar functional domain structure: a variable N-terminal region, which is involved in modulation of gene expression; a short well-conserved DNA-binding domain, which is crucial for recognition of specific DNA sequences and for receptor dimerization; and a partially conserved C-terminal ligand-binding domain, which is important for hormone binding and also for receptor dimerization and transactivation.

[Brinkman, A. O., "Steroid Hormone Receptors: Activators of Gene Transcription," *J. Ped. Endocrinol.*, 7(4): 275 (1994).]

Lehrer et al., *The Lancet*, 335: 622 (Mar. 17, 1990) sets forth a schematic representation of the human estrogen receptor gene, denoting six regions denoted A-F. The exact function of region A from the N-terminus is unknown according to Lehrer et al. Region B plays a part in transcription enhancement of ER-regulated genes. Region C is the DNA-binding domain. Region D is a hinge region. Region E is the hormone binding domain. The function of the C-terminal region F is unknown according to Lehrer et al.

Beato, M., "Gene Regulation by Steroid Hormones," *Cell*, 56: 335 (Feb. 10, 1989), divides the steroid/thyroid hormone receptors in accordance with their structure and function into the follow ing two sub-groups: (1) glucocorticoid, progesterone, androgen, and mineralocorticoid receptors; and (2) estrogen, thyroid hormone, retinoic acid, and vitamin D3 receptors. Those listed steroid/thyroid hormone receptors are preferred nuclear receptor analytes according to this invention. More preferred as analytes are PR and ER, and most preferred is ER.

Nucleic Acid Reagents

The nucleic acid reagents of this invention may be single-stranded or double-stranded, preferably double-stranded, and contain one or more response element segments, preferably one to fifteen response element segments, more preferably one to ten response element segments, still more preferably from one to eight response element segments, and even more preferably from four to eight response element segments. The nucleic acid reagent may also contain one or more oligonucleotide segments, preferably at one or both ends of the reagent, that are complementary to a segment of a nucleic acid multimer for use in a signal amplification system as described in detail below.

Alternatively, the nucleic acid reagent may contain one or more oligonucleotide segments that carry a detectable marker as detailed below. Further alternatively, said one or more oligonucleotide segments can be single-stranded, preferably at one or both ends of the nucleic acid reagent, and complementary to an oligomer probe that carries a detectable marker.

The nucleic acid reagents are preferably DNA, and can be isolated from naturally occurring sources or can be prepared recombinantly or synthetically; preferably they are prepared synthetically. It is preferred that when there is more than one response element segment in a nucleic acid reagent, that the core sequences of said response elements be the same; whereas the spacer sequences and flanking sequences may vary. Preferably the flanking sequences are naturally occurring sequences that are AT-rich. Still more preferably, when there are more than one response element segment in the nucleic acid reagents of this invention, those response elements are copies of each other, for example, dimers, trimers, tetramers, pentamers, hexamers, septamers, octamers, etc., still more preferably tandem repeats.

Table 1 below lists representative consensus response element segments and sequences containing core sequences to which a number of nuclear receptors bind. Information in Table 1 is primarily from Beato, M., id.; Locker and Buzard, "A dictionary of transcription control sequences," J. DNA Sequencing and Mapping, 1: 3 (1990); Peale et al., Biochemistry, 28(2): 8671 (Oct. 31, 1989); Anolik et al., Biochemistry, 34: 2511 (1995); and Anolik et al., J. Steroid Biochem. Molec. Biol., 46(6): 713 (1993).

TABLE 1

RESPONSE ELEMENT SEQUENCES FOR NUCLEAR RECEPTORS

| | | |
|---|---|---|
| GRE (+) (positive modulation) | GGTACANNNTGTTCT | [SEQ. ID. NO.: 2] |
| PRE | " | |
| ARE | " | |
| MRE | " | |
| ERE | AGGTCANNNTGACCT | [SEQ. ID. NO.: 3] |
| EcRE | AGGGTTNNNTGCACT | [SEQ. ID. NO.: 4] |
| TRE | TCAGGTCA---TGACCTGA | [SEQ. ID. NO.: 5] |
| RRE | " | |
| GRE (−) (represses) | ATYACNNNNTGATCW | [SEQ. ID. NO.: 6] |
| ERE (consensus) | CCA<u>GGTCA</u>GAG<u>TGACC</u>TGA GCTAAAATAACACATTCAG | [SEQ. ID. NO.: 7] |
| ERE (consensus) | <u>GGTCA</u>GAG<u>TGACC</u> | [SEQ. ID. NO.: 8] |
| ERE (consensus) | <u>GGTCA</u>NNN<u>TGACC</u> | [SEQ. ID. NO.: 9] |
| ERE (consensus) | GGTCACAGTGACC | [SEQ. ID. NO.: 10] |
| T₃RE | AGGTAAGATCAGGGACGT | [SEQ. ID. NO.: 11] |
| ERE (core seq. for human oxytocin) | <u>GGTGACCTTGACC</u> | [SEQ. ID. NO.: 12] |
| ERE (core seq. for human c-fos) | CGGCAGC<u>GTGACC</u> | [SEQ. ID. NO.: 13] |
| ERE (core seq. for human prolactin) | T<u>GTCACC</u>TT<u>GGCC</u> | [SEQ. ID. NO.: 14] |

Although the above sequences are listed as single-stranded, it is understood that the complementary strands are preferably present when they or related sequences are incorporated into nucleic acid reagents used in the methods of this invention. Thus, the nucleic acid reagents may be double-stranded or single-stranded; preferably, they are double-stranded.

The consensus sequences are based on base pair conservation in functional response elements, and the base at each position is that present in the majority of such response elements for a particular nuclear receptor. However, variations from the consensus sequences are included within the concept of response element segments which are herein considered to contain at least a core sequence and spacer nucleotides between the inverted repeats of the core sequence for a particular response element.

Variations from the consensus sequence for response elements are known. For example, a comparison of the EREs from the estrogen responsive genes sequenced to date is shown in Table 5 at page 726 of Anolik et al., *J. Steroid Biochem. Molec. Biol*, 46(6): 713 (1993) and show that the core sequences differ by one or two nts from the core consensus sequence for ERE [SEQ. ID. NO.: 9] for many estrogen responsive genes. Such a comparison can be made herein among ERE core sequences that are underlined for SEQ. ID. NOS.: 7–10 and 12–14 in Table 1. The underlined portions of SEQ. ID. NOS.: 7–10 show the consensus core sequence for ERE. Thus, such variations are known in the art, and the term "response element segment" or "response element core sequence" are considered to include such variations from consensus sequences known for particular response elements.

The average size of response elements, as defined above, is in the vicinity of from about 30 bp to about 50 bp, more typically from about 35 bp to about 45 bp. Core sequences of response elements with varying spacer nucleotides separating the inverted repeats of the core sequences are in the vicinity of 12 to 18 bp, more particularly from about 13 to 15 bp.

A response element segment as the term is used herein represents a segment of a response element which comprises at least the core sequence of the response element and the spacer nucleotides between the inverted repeats for example, 5'-GGTCAnnnTGACC-3' [SEQ. ID. NO.: 9] for the ERE. However, more preferably said one or more ERE segments in an ER-specific nucleic acid reagent contain naturally occurring flanking sequences, preferably AT-rich flanking regions, more preferably 3' AT-rich flanking regions. Flanking sequences are herein considered to be important in providing specificity and affinity for binding of the activated receptor, for example, receptor/ligand complexes, to a response element segment.

Anolik et al., *Biochem.*, 34: 2511 (1995), postulate that naturally occurring ERE flanking sequences, such as an AT-rich region, bestow upon the ERE sequence enhanced binding capacity to an ER/ligand (estradiol) complex. Thus, it is preferred that the nucleic acid reagents of this invention contain ERE segments, such as SEQ. ID. NO.: 7, which contain at least one AT-rich region flanking the core sequences.

Anolik et al. go on to postulate at page 2512 "that the number, spacing and sequences of EREs can produce fine tuning of the response of individual genes to increasing estrogen levels in vivo, through variations in the degree of cooperative binding." Anolik et al. demonstrate that ERE flanking sequences are essential for cooperative binding of ER to stereoaligned EREs.

A representative and preferred nucleic acid reagent according to this invention for assaying ER is SEQ. ID. NO.: 1 which is an octamer of the 38 bp ERE segment shown above as SEQ. ID. NO.: 7 Also preferred as a nucleic acid reagent for assaying ER are a monomer, dimer trimer or tetramer of SEQ. ID. NO.: 7 with above-noted variations optimized to enhance the reagent's binding capacity to activated ER, ligand-occupied or otherwise activated.

It is preferred that synthetically prepared nucleic acid reagents are DNA reagents, and that if a binding pair is used to link a detectable marker to the reagent, that during synthesis one partner of the binding pair is incorporated into the reagent either randomly or selectively, but preferably not within any core response element sequences of the nucleic acid reagent. Preferably, such incorporation occurs at multiple sites, and preferably selectively, for example at the 5' phosphorylated ends and/or at other sites not within the core response element sequences.

Recent evidence indicates that a thyroid hormone receptor (TR) binds to each of two hexamer half-sites, comprising a core consensus sequence of AGGTCA. TRs can bind to thyroid response elements (TREs) as monomers, homodimers, and heterodimers with nuclear proteins such as T3 receptor auxiliary protein(s) (TRAP) and retinoid-X receptors. [Ikeda et al., Endocrinol., 135(4) 1628 (1994).]

Antibodies to Nuclear Receptors

Antibodies useful in the assays of this invention are antibodies to functional nuclear receptors, that is, antibodies that are capable of binding specifically to activated receptors, whether ligand-occupied or otherwise activated, that are capable of binding to their specific response element. As illustrated below, anti-receptor antibodies are selected for the assays of this invention by a screening process to assure that the selected antibodies that are specific for a certain nuclear receptor form immunocomplexes with that nuclear receptor when it is bound to its response element. Specifically herein illustrated is a screening process for anti-ER antibodies that are screened for ER/ligand (estradiol)/ERE immunocomplexes, that is, wherein ER is activated by being ligand-occupied.

A preferred screening process employs a gel supershift assay as illustrated herein. Thus, from the lists of antibodies provided herein, whether polyclonal, monoclonal or antibody fragments, only antibodies that pass a screening test to assure that they are capable of specifically binding to activated functional receptors that are bound to their respective response elements are used in the assays of this invention.

Listed below are exemplary antibodies to a variety of nuclear receptors. It is understood by those of skill in the art that from those representative antibodies and from other antibodies to nuclear receptors known in the art, antibodies can be selected by such screening procedures to find suitable antibodies for the assays of this invention.

In general, preferred polyclonal and monoclonal antibodies to nuclear receptors for use in assays according to this invention are directed against the N-terminal region or the C-terminal region of the receptors and are not directed against the DNA-binding domain. If ligand is used to activate the receptors, the antibodies should be selected outside the ligand binding domain as well as outside the DNA binding domain.

A variety of antibodies, both polyclonal and monoclonal, which bind to specific nuclear receptors are known and can be screened to determine if they would be useful in the methods of this invention. Exemplary polyclonal and monoclonal antibodies prepared against ER and PR are set forth below under separate sub-headings.

Other exemplary antibodies that can be screened for use in the assays of this invention to detect, or detect and quantitate functional nuclear receptors include, for example, polyclonal antibodies raised against partially purified preparations of GR [Okret et al., *Biochem. Biophys. Acta.,* 671: 205 (1981); Eisen, *PNAS* (USA) 77: 3893 (1980); and Govindan, *J. Steroid Biochem,* 11: 323 (1979)], and autoimmune antibodies to androgen receptor found in human serum [Liao and Witte, *PNAS,* 82: 8345 (1985)].

Polyclonal antibodies known to react with human GR prepared against a 26 amino acid (aa 150–175) synthetic peptide whose sequence is from the N-terminal region of human GR are available from Affinity BioReagent [Golden, Colorado (USA); PA1-510; Srivastava et al., *Endocrinol,* 127: 1770 (1990)]. Polyclonal antibodies that react with human, rat and mouse GR prepared respectively against a 22 amino acid (aa 346–367) synthetic peptide and a 15 amino acid (aa 245–259) synthetic peptide whose sequences are from the N-terminal region of human GR are also available from Affinity BioReagent [PA1-511 and PA1-512; Cidlowski et al., *Mol. Endocrinol.,* 4: 1427 (1990)]. Other monoclonal antibodies against GR are known, such as, those described in Grandics et al., *Endocrinology,* 111: 1731 (1982); Okret et al., *PNAS,* 81: 1609 (1984); Westphal et al., *EMBO J.,* 1: 1467 (1982); and Logeat et al., *PNAS,* 80: 6456 (1983).

Polyclonal antibodies which react specifically with human, rat and mouse MR but not GR, which were prepared against a 10 amino acid (aa 87–96) synthetic peptide whose sequence is from the N-terminal region of human MR are available from Affinity BioReagent [PA1-610; Alnemri et al., *J. Biol. Chem.* 266: 18072 (1991)].

Monoclonal and polyclonal antibodies prepared against synthetic peptides from the C-terminal regions of mouse RR alpha and mouse RR beta are also available from Affinity BioReagent [MA1-810 and MA1-811; PA1-810 and PA1-811].

Polyclonal antibodies against TR, alpha 1, TR, alpha 1 (TRa-1-403), TR, alpha 2 (TRa-2-431), TR, alpha (TRa-144), TR, beta 1 (TRβ-62) and TR, beta (TRβ-117) prepared against synthetic peptides respectively from the extreme C-terminal of human TRa-1 (aa 403–410); from the extreme C-terminal of human TR-alpha 1 (aa 403–410); from the C-terminal of the human TR (aa 431–451); from the Nterminal region of the human TR-alpha (aa 144–162); the N-terminal region of the human TR-beta-1 (aa 62–82); and from the N-terminal region of the human TR (aa 117–138), are also available from Affinity BioReagent under the product numbers PA1-210 to 214.

Monoclonal antibodies to vitamin D receptor are available from the American Type Culture Collection [HB-9496; Rockville, Md. (USA)]; from Biogenesis Inc. [9580-3006; Sandown, N. H. (USA)]; and MAbs directed against the region C-terminal to the DNA-binding domain of human vitamin D receptor (aa 89–105) are available from Affinity BioReagent (MA1-710).

Antibodies to ER

A variety of different polyclonal antibodies have been prepared against ER protein. Exemplary are Raam et al., *Mol. Immunol.,* 18: 143 (1981); Greene et al., *J. Ster. Biochem.,* 11: 333 (1979); Greene et al., *PNAS* (USA), 74: 3681 (1977); Jensen et al., U.S. Pat. No. 4,232,001 (issued Nov. 4, 1980); Radanyi et al., *Acad. Sci. Paris Ser. D.,* 288: 255 (1979); and Coffer et al., *Biochem. Internal.* 1: 126 (1980).

Also a large variety of monoclonal antibodies that specifically bind to human and animal ER proteins are known. Exemplary are Greene et al., "Monoclonal antibodies to estrophilin: Probes for the study of estrogen receptors," *PNAS* (USA), 77: 157 (1980); Greene et al., "Monoclonal antibodies to human estrogen receptor," *PNAS* (USA) 77: 5115 (1980); Greene and Press, "Immunochemical evaluation of estrogen receptor and progesterone receptor in breast cancer," In: *Immunological Ap proaches to the Diagnosis and Therapy of Breast Cancer,* pp. 119–135 [Ceriant, R.L., ed.; Plenum Press, N.Y. (1987); King et al., "Comparison of immunocytochemical and steroid-binding assays for estrogen receptor in human breast tumors," *Cancer Res.,* 45: 283 (1985); King and Greene, "Monoclonal antibodies localize estrogen receptor in the nuclei of target cells," *Nature,* 307: 745 (1984); Press and Greene, "An immunocytochemical method for demonstrating estrogen receptor in human uterus using monoclonal antibodies to estrophilin," *Lab. Invest.,* 50: 480 (1984); Borgna et al., *Biochem.,* 23: 2162 (1984); Fauque et al., *J. Biol. Chem.,* 260: 15547 (1985); and Monocharmont et al., *Biochem.,* 23: 3907 (1984).

Particularly preferred anti-ER antibodies are those directed to the N-terminal transactivation domain, more preferably to amino acids 122 to 180 of said domain. Traish et al., *Steroids,* 60: 467 (1995), describe preparing polyclonal antibodies to peptides spanning the amino acid sequences between 140–154, between 155–169 and 170–185 of human ER, and a monoclonal antibody to the peptide from 140–154 of the human ER amino acid sequence. Those polyclonal antibodies and that monoclonal antibody, especially the monoclonal antibody, are preferred anti-ER antibodies according to this invention.

Antibodies to PR

A variety of different polyclonal antibodies have been prepared against native and fractionated PR proteins, and against the nuclear binding PR complex. Exemplary are Tuohimaa et al., *Biochem. Biophys. Res. Comm.,* 119: 433 (1984); Renoir et al.. *Eur. J. Biochem.,* 324: 1 (1982); Gronemeyer et al., *J. Biol. Chem.,* 260: 6916 (1985); Smith et al., *Endocrinol.,* 122: 2816 (1988); Smith et al., *J. Steroid Biochem.,* 30: 1 (1988); Welgel et al., *Endocrinol.,* 125: 2494 (1989); Greene, U.S. Pat. No. 4,742,000 (issued May 3, 1988); Logeat et al., *PNAS* (USA), 78: 1426 (1981); Feil et al., *Endocrinol,* 112: 396 (1983); and Renoir et al., *Eur. J. Biochem.,* 127: 81 (1982).

Also, monoclonal antibodies against human and animal PR proteins and complexes have been prepared. Exemplary are Loosefelt et al., *PNAS* (USA), 83: 9045 (1986); Sullivan et al., *Endocrinol.,* 119: 1549 (1986); Clark et al., *Endocrinol,* 121: 1123 (1987); Nakoa et al., *Can. J. Biochem. Cell Biol..* 63: 33 (1985); Hendler and Yuan, *Cancer Res.,* 45: 421 (1985); and Greene, U.S. Pat. No. 4,742,000 (issued May 3, 1988).

Analogously to anti-ER antibodies, preferred anti-PR antibodies are those directed to either the N-terminal or C-terminal regions and not to the DNA-binding domain. Again, if ligand is used to activate the receptors, the antibodies should be selected outside the ligand binding domain as well as outside the DNA-binding domain. Particularly preferred are anti-PR monoclonal antibodies directed against the N-terminal region, particularly the transactivation domain, that does not include any portion of the DNA-binding domain.

Solid Phase

The solid phase used in the assays of this invention may be any surface commonly used in immunoassays. For example, the solid phase may be particulate; it may be the surface of beads, for example, glass or polystyrene beads; or it may be the solid wall surface of any of a variety of containers, for example, centrifuge tubes, columns, microtiter plate wells, filters, membranes and tubing, among other containers.

When particles are used as the solid phase, they will preferably be of a size in the range of from about 0.4 to 200 microns, more usually from about 0.8 to 4.0 microns. Magnetic or magnetizable particles are a preferred particulate solid phase, and microtiter plate wells are a preferred solid wall surface. Magnetic or magnetizable particles may be particularly preferred when the steps of the methods of this invention are performed in an automated immunoassay system.

Sample Size

An important aspect of the invention is to provide highly sensitive assays, such that a very small amount of tissue or cells is required to prepare a sample to be assayed. A small sample size is especially important when it is to be prepared from biopsied tissue or from a cell suspension taken from a cancer patient or person suspected of having cancer. It is preferred that minimally invasive techniques, such as, fine needle aspirations or stereotactic needle biopsies be used, which are possible techniques when the amount of the sample required for an assay is small. Further, a small sample size can have the advantage of minimizing the amount of sample preparation time involved, for example, minimizing the time spent in pulverizing and grinding biopsied tissue, or eliminating the necessity for such pulverizing/grinding, and thereby providing quicker results.

Therefore, it is an object of this invention to achieve a sensitivity in the assays allowing for a tissue sample size of less than 50 mg, more preferably less than 35 mg, even more preferably less than 25 mg, still more preferably in the range of from about 10 mg to 25 mg, further more preferably from about 5 mg to 15 mg, and even more preferably in a range of from about 1 mg to about 10 mg. To achieve such small sample sizes for successful analyses according to this invention, highly sensitive assays are required, and are effected by the formats of the instant assays, and by the use of sensitive detection, or detection and quantitation systems.

Preferred detection/quantitation systems of this invention are luminescent, and more preferred is the use of a luminescent detection/quantitation system in conjunction with a signal amplification system. Exemplary luminescent labels, preferably chemiluminescent labels, are detailed below, as are preferred signal amplification systems.

Especially preferred is a signal amplification system used when it is the nucleic acid reagent that is the tracer component. In such a system, the nucleic acid reagent has one or more oligonucleotide segments which are complementary to a first segment on a nucleic acid multimer; then, labeled oligonucleotides in turn hybridize to a multiplicity of complementary second oligonucleotide segments on said nucleic acid multimer. That system is explained in detail below under the heading Signal Amplification System.

Signal Detection/Ouantitation Systems

The complexes formed by the assays of this invention can be detected, or detected and quantitated by any known detection/quantitation systems used in immunoassays and/or nucleic acid hybridization assays. As appropriate, the antibodies and nucleic acid reagents of this invention used as tracers may be labeled in any manner directly or indirectly, that results in a signal that is visible or can be rendered visible.

Detectable marker substances include radionuclides, such as $^3H$, $^{125}I$, and $^{131}$; fluorescers, such as, fluorescein isothiocyanate and other fluorochromes, phycobiliproteins, phycoerythine, rare earth chelates, Texas red, dansyl and rhodamine; calorimetric reagents (chromogens); electron-opaque materials, such as colloidal gold; bioluminescers; chemiluminescers; dyes; enzymes, such as, horseradish peroxidase, alkaline phosphatase, glucose oxidase, glucose-6-phosphate dehydrogenase, acetylcholinesterase, α-, β-galactosidase, among others; coenzymes; enzyme substrates; enzyme cofactors; enzyme inhibitors; enzyme subunits; metal ions; free radicals; or any other immunologically active or inert substance which provides a means of detecting or measuring the presence or amount of immunocomplex formed. Exemplary of enzyme substrate combinations are horseradish peroxidase and tetramethyl benzidine (TMB), and alkaline phosphatase and paranitrophenyl phosphate (pNPP).

Preferred detection, or detection and quantitation systems according to this invention produce luminescent signals, bioluminescent (BL) or chemiluminescent (CL). In chemiluminescent (CL) or bioluminescent (BL) assays, the intensity or the total light emission is measured and related to the concentration of the unknown analyte. Light can be measured quantitatively using a luminometer (photomultiplier tube as the detector) or charge-coupled device, or qualitatively by means of photographic or X-ray film. The main advantages of using such assays is their simplicity and analytical sensitivity, enabling the detection and/or quantitation of very small amounts of analyte.

Exemplary luminescent labels are acridinium esters, acridinium sulfonyl carboxamides, luminol, umbelliferone, isoluminol derivatives, photoproteins, such as aequorin, and luciferases from fireflies, marine bacteria, Vargulla and Renilla. Luminol can be used optionally with an enhancer molecule, preferably selected from the group consisting of 4-iodophenol or 4-hydroxycinnamic acid. Acridinium esters are one of the preferred types of CL labels according to this invention. A signal is generated by treatment with an oxidant under basic conditions.

Also preferred luminescent detection systems are those wherein the signal (detectable marker) is produced by an enzymatic reaction upon a substrate. CL and BL detection schemes have been developed for assaying alkaline phosphatase (AP), glucose oxidase, glucose 6-phosphate dehydrogenase, horseradish peroxidase (HRP), and xanthine-oxidase labels, among others. AP and HRP are two preferred enzyme labels which can be quantitated by a range of CL and BL reactions. For example, AP can be used with a substrate, such as an adamantyl 1,2-dioxetane aryl phosphate substrate (e.g. AMPPD or CSPD; [Kricka, L. J., "Chemiluminescence and Bioluminescence, Analysis by," at p. 167, *Molecular Biology and Biotechnology: A Comprehensive Desk Reference* (ed. R. A. Meyers) (VCH Publishers; N.Y., N.Y.; 1995)]; preferably a disodium salt of 4-methoxy-4-(3-phosphatephenyl)spiro [1,2dioxetane-3,2'-adamantane], with or without an enhancer molecule, preferably, 1-(trioctylphosphonium methyl)-4 (tributylphosphonium methyl) benzene diochloride. HRP is preferably used with substrates, such as, 2', 3', 6'-trifluorophenyl 3-methoxy-10-methylacridan-9-carboxylate.

CL and BL reactions can also be adapted for analysis of not only enzymes, but other substrates, cofactors, inhibitors, metal ions and the like. For example, luminol, firefly luciferase, and marine bacterial luciferase reactions are indicator reactions for the production or consumption of peroxide, ATP, and NADPH, respectively. They can be coupled to other reactions involving oxidases, kinases, and dehydrogenases, and can be used to measure any component of the coupled reaction (enzyme, substrate, cofactor).

The detectable marker may be directly or indirectly linked to the antibody or the nucleic acid reagent used in an assay of this invention. Exemplary of an indirect linkage of the detectable label is the use of a binding pair between the antibody or nucleic acid reagent and the marker, or the use of a signal amplification signal, such as those described below.

Exemplary of binding pairs that can be used to link antibodies or nucleic acid reagents of assays of this invention to detectable markers are biotin/avidin, streptavidin, or anti-biotin; avidin/anti-avidin; thyroxine/thyroxine-binding globulin; antigen/antibody; antibody/anti-antibody; carbohydrate/lectins; hapten/anti-hapten antibody; dyes and hydrophobic molecules/hydrophobic protein binding sites; enzyme inhibitor, coenzyme or cofactor/enzyme; polynucleic acid/homologous polynucleic acid sequence; fluorescein/anti-fluorescein; dinitrophenol/ anti-dinitrophenol; vitamin B12/intrinsic factor; cortisone, cortisol/cortisol binding protein; and ligands for specific receptor protein/membrane associated specific receptor proteins. Preferred binding pairs acording to this invention are biotin/avidin or streptavidin, more preferably biotin/streptavidin.

It is further preferred that when the nucleic acid reagent is the tracer component that it is biotinylated. Said nucleic acid reagents can be biotinylated randomly or selectively at one or multiple sites, preferably at multiple sites, more preferably selectively at multiple sites, still more preferably selectively at the 5' phosphorylated ends and/or at multiple sites that are not within the core sequence of the response element segments.

Various means for linking labels directly or indirectly to antibodies and nucleic acids are known in the art. For example, labels may be bound either covalently or non-covalently. Exemplary antibody conjugation methods are described in: Avarmeas et al., *Scan. J. Immunol.,* 8 (Suppl. 7): 7 (1978); Bayer et al., *Meth. Enzymol.,* 62: 308 (1979); Chandler et al., *J. Immunol. Meth.,* 53: 187 (1982); Ekeke and Abuknesha, *J. Steroid Biochem.,* 11: 1579 (1979); Engvall and Perlmann, *J. Immunol.,* 109: 129 (1972); Geoghegan et al., *Immunol. Comm.,* 7: 1 (1978); and Wilson and Nakane, *Immunofluorescence and Related Techniques, p.* 215 [Elsevier/North Holland Biomedical Press; Amsterdam (1978)].

Exemplary nucleic acid labeling techniques also include the incorporation of radioactive labels, e.g., Harper et al. *Chromosoma,* 83: 443 (1984); direct attachment of fluorochromes or enzymes, e.g., Smith et al., *Nucleic Acids Research,* 13: 2399 (1985), and Connolly et al., *Nucleic Acids Research,* 13: 4485 (1985); and various chemical modifications of nucleic acids that render them detectable immunochemically or by other affinity reactions, e.g., Tchen et al., "Chemically Modified Nucleic Acids as Immunodetectable Probes in Hybridization Experiments," *PNAS,* 81: 3466 (1984); Richardson et al., "Biotin and Fluorescent Labeling of RNA Using T4 RNA Ligase," *Nucleic Acids Research,* 11: 6167 (1983); Langer et al., "Enzymatic Synthesis of Biotin-Labeled Polynucleotides: Novel Nucleic Acid Affinity Probes," *PNAS,* 78: 6633 (1981); Brigati et al., "Detection of Viral Genomes in Cultured Cells and Paraffin-Embedded Tissue Sections Using Biotin-Labeled Hybridization Probes," *Virology,* 126: 32 (1983); Broker et al., "Electron Microscopic Visualization of tRNA Genes with Ferritin-Avidin: Biotin Labels," *Nucleic Acids Research,* 5: 363 (1978); Bayer et al., "The Use of the Avidin Biotin Complex as a Tool in Molecular Biology," *Methods of Biochemical Analysis,* 26: 1 (1980); Langer-Safer et al., *PNAS,* 79: 4381 (1982); Landegent et al., *Exp. Cell Res.,* 153: 61 (1984); Leary et al., *PNAS* (USA), 80: 4045 (1983); Renz and Kurz, *Nucleic Acids Res.,* 12: 3435 (1984); and Richardson and Gumport, *Nucleic Acids Res.,* 11: 6167 (1983).

Depending upon the nature of the label, various techniques can be employed for detecting, or detecting and quantitating the label. For fluorescers, a large number of fluorometers are available. For chemiluminescers, luminometers or films are available. With enzymes, a fluorescent, chemiluminescent, or colored product can be determined or measured fluorometrically, luminometrically, spectrophotometrically or visually.

Signal Amplification Systems

Preferred for use in the assays of this invention is a detectable marker that provides a signal that is amplifiable so that functional nuclear receptors can be detected, or detected and quantitated at very low levels, and so that, thus, only very small amounts of a sample need to be assayed. Exemplary and preferred is the use of a signal amplification system which produces a high reproducible signal-to-noise ratio, low nonspecific binding, and employs a universal signal moiety that is capable of specifically binding to the nuclear receptor complexes identified according to this invention at very low concentrations to form a stable complex that can then be detected, or detected and quantitated.

Such signal amplification systems are well known in the art. Exemplary of one such signal amplification system is that illustrated schematically in FIG. 1, wherein a nucleic acid reagent containing a hormone response element (HRE) segment is biotinylated at each end. Then streptavidin conjugated to HRP, a universal signal moiety, is incubated with the anti-receptor/receptor/ligand/biotinylated nucleic acid reagent complex on the solid phase; and the streptavidin binds with biotin on the nucleic acid reagent and complexes stably with the other solid phase complexed components. After removing any noncomplexed components, a HRP substrate, TMB in FIG. 1, is added, then a stop reagent, and the enzymatic reaction product is detected, or detected and quantitated.

Preferably, the signal from the system illustrated in FIG. 1 would be further amplified by using a nucleic acid reagent that is biotinylated at multiple sites, randomly or selectively, preferably at sites other than within the core sequences of the response element segments to which the nuclear receptor under assay binds. The nucleic acid reagent is preferably biotinylated during its synthesis when prepared synthetically at a maximum number of sites other than within the core sequences. Of course, binding pairs other than biotin and streptavidin, as listed above, can be used, as well as, other enzymes, for example, alkaline phosphatase among others. Chemiluminescent substrates are preferred for use in such signal amplification systems.

Another preferred signal amplification system for use in the assays of this invention is based on an amplifier system disclosed in, for example, Urdea et al., U.S. Pat. No. 5,124,246 (issued Jun. 23, 1992) entitled "Nucleic Acid Multimers and Amplified Nucleic Acid Hybridization Assays Using Same," and in Kolberg et al., U.S. Pat. No. 5,407,795 (issued Apr. 18, 1995) entitled "CMV Probes for Use in Solution Phase Sandwich." When such a system is used, the nucleic acid reagent containing one or more response element segments to which the nuclear receptor under assay binds, also comprises one or more nt segments that is or are complementary to an oligonucleotide unit on a nucleic acid multimer. Said nucleic acid multimer, as described in the above-cited patents, contains also a multiplicity of second oligonucleotide units that are complementary to an oligonucleotide that is labeled directly or indirectly. Said nucleic acid multimer is preferably branched wherein the multiplicity of second oligonucleotide units form the branches, and the oligonucleotide unit complementary to one or more segments on the nucleic acid reagent is the trunk. Further, said branched nucleic acid multimers are preferably branched DNA multimers.

Thus, that signal amplification system can be envisioned wherein the solid phase antibody/nuclear receptor/ligand/nucleic acid reagent complex has been formed, and uncomplexed components have been removed; the nucleic acid multimer is then added under hybridizing conditions and binds to the nucleic acid reagent at complementary site(s) forming a stable complex. Thereafter, uncomplexed multimers are removed, and oligonucleotides labeled directly or indirectly, that are complementary to the multiplicity of second oligonucleotide units on the nucleic acid multimer, are contacted with the solid phase complex under hybridizing conditions. Unbound labeled oligonucleotides are then removed, and signal from any label on the solid phase complex product is detected, or detected and quantitated. The signal from any label on the solid phase complex is correlated with the presence of nuclear receptors under assay that are functional, or the amount of signal from label on the solid phase is correlated with the amount of nuclear receptors under assay that are functional.

Any of the detectable markers outlined above can be used in accordance with the knowledge of those skilled in the art in such signal amplification systems, directly or indirectly, for example, using the above-outlined binding pairs or enzymatic reactions. Various means for providing labels bound to nucleic acid sequences have been reported as in the exemplary citations listed above.

Preferred labels are chemiluminescent for example wherein chemiluminescence is produced by an enzymatic reaction. Exemplary chemiluminescers, enzymes and substrates are detailed above.

The hybridization steps of such a signal amplification system using nucleic acid multimers generally take from about 10 minutes to 2 hours and can be carried out at a mildly elevated temperature, generally in the range from about 20° C. to 80° C., more usually from about 35° C. to 70° C., particularly 35° C. to 45° C. The stringency of the hybridization medium may be controlled by temperature, salt concentration, solvent system, and the like. Thus, the stringency may be varied depending upon the target sequence on the nucleic acid reagents of this invention.

The oligonucleotide units of the nucleic acid multimer and of the segment of the nucleic acid reagent complementary to said first oligonucleotide unit are preferably at least 15 nucleotides (nts), usually at least 25 nts, and preferably not more than 50 nts.

The nucleic acid multimers can be linear or branched polymers of the same repeating single-stranded oligonucleotide unit or different single-stranded oligonucleotide units. As indicated above, the nucleic acid multimers are preferably branched (as described in Kolberg et al., id), and preferably the repeated oligonucleotide units are the same. The oligonucleotide units of the multimer may be composed of RNA, DNA, modified nucleotides or combinations thereof. Preferably, such oligonucleotide units of the multimer are DNA for the purposes of the instant assays.

The following examples further illustrate the invention. The examples are not meant to limit the invention in any way.

EXAMPLE 1

This example provides a representative assay of this invention to detect, or detect and quantitate functional ER from cytosolic preparations. The preferred embodiment illustrated schematically in FIG. 1 is the general format for the assay described in this example.

Materials

Estrogen Receptor. The ER-positive and negative controls were from Diagnostic Systems Laboratories (DSL), Webster, Tex. (USA), and Du Pont, Boston, Mass. (USA). Calf uteri were obtained from Animal Technologies, Tyler, Tex. (USA).

Antibody. The ER monoclonal antibody (MAb) was from the Department of Biochemistry at Boston University in Boston, Mass. (USA).

ERE. A plasmid [Z16.0121] containing a tandem octamer of a 38 bp estrogen response element (ERE) consensus sequence segment, was kindly provided by Drs. Carolyn M. Klinge, Robert A. Bambara, and Russell Hilf of the Department of Biochemistry at the University of Rochester School of Medicine and Dentistry, Rochester, N.Y. (USA). The sequence of said ERE octamer [SEQ. ID. NO.: 1] is as follows:

CCAGGTCAGAGTGACCTGAGCTAAAATAACACATTCAGCCAGGT
CAGAGTGACCTGAGCTAAAATAACACATTCAGCCAGGTCAGAGT
GACCTGAGCTAAAATAACACATTCAGCCAGGTCAGAGTGACCTG
AGCTAAAATAACACATTCAGCCAGGTCAGAGTGACCTGAGCTAA
AATAACACATTCAGCCAGGTCAGAGTGACCTGAGCTAAAATAAC
ACATTCAGCCAGGTCAGAGTGACCTGAGCTAAAATAACACATTC
AGCCAGGTCAGAGTGACCTGAGCTAAAATAACACATTCAG.

The ERE octamer represents eight tandem (head-to-tail) copies of a 38 bp consensus ERE sequence [SEQ. ID. NO.: 7] as follows: 5' CCA <u>GGTCAGAGTGACC</u>TGAGCTAAAATAACACATTCAG 3'. That 38 bp (double stranded) sequence was cloned (blunt ended) in the reverse orientation into the SmaI site of pGEM-7Zf(+) [Promega (Madison, Wis.; USA); see Pearle et al., *Biochemistry*, 28 (22): 8671 (31 Oct., 1989)]. The underlined nucleotides represent a core consensus ERE [13 bp inverted repeat wherein the three internal nts (GAG) act as spacers] [SEQ. ID. NO.: 8], and the 3' half of the consensus ERE is AT-rich.

Patient Samples. Breast cancer cytosols, previously tested by the Abbott ER EIA Monoclonal Kit, were obtained from the University of Oregon Health Sciences Center in Portland, (USA).

Other Assay Reagents/Components. Corning microtiter strip wells were from VWR Scientific [San Francisco, Calif. (USA)]. AH-BNHS (amino hexanoyl-biotin-N-hydroxysuccinimide ester) was from Zymed [South San Francisco, Calif. (USA)], and NAP-5 columns were from Pharmacia [Piscataway, N.J. (USA); Uppsala, Sweden]. ImmunoPure Plus immobilized Protein-A and OligoLink derivatization kit for phosphorylated oligonucleotides were from Pierce Chemical Co. [Rockford, Ill. (USA)]. The $^{125}$I-ER ligand binding assay kit was from Diagnostic Systems Laboratories (DSL) [Webster, Tex. (USA)], and all other reagents including streptavidin-HRP and estradiol were from Sigma Chemical Company [St. Louis, Mo. (USA)]. For the assay buffer, 50 mM Tris, pH 7.4, 1% BSA, 1 mM EDTA, 0.1M KCl and 10% glycerol were used. Phosphate-buffered saline (PBS) containing 0.05% Tween-20 was used as the wash buffer.

Methods

Purification of ER Antibody. The ER MAb was purified, using Protein-A immobilized on agarose beads, following the procedure recommended by the manufacturer (Pierce). Purity was confirmed by SDS-PAGE analysis, using the Pharmacia Phast Gel System.

Preparation of ER Antibody-Coated Microtiter Wells. Microtiter strip wells were coated, overnight at 40° C., with 250 ng (200 μl) of purified ER antibody. They were washed with wash buffer and blocked with 1% BSA for 2 hr at room temperature. The wells were washed again as above followed by a final wash with 1% dextrose and placed in a drying chamber (relative humidity less than 15%) until thoroughly dry (16–24 hr). Strip wells were then stored in Mylar Zip-Lock bags with desiccant at 4° C. until used.

Purification of Plasmid DNA. The plasmid DNA containing the ERE octamer [SEQ. ID. NO.: 1] was resuspended in a small volume (20–50 μl) TE buffer, and then transfected into *E. coli* strain DH5α for amplification by the Molecular Biology Group at CCD in Alameda, Calif. (USA). The amplified plasmid was purified by a modified alkali lysis procedure and cleaved by restriction enzymes. The ERE fragment was separated from the rest of the plasmid by PEG precipitation. The final ERE product was about 95% pure by agarose gel electrophoresis analysis.

Preparation of Biotinylated ERE. The ERE octamer was biotinylated either selectively at the 5'-phosphorylated end, using the Pierce OliogoLink Kit, or by random labeling. Conjugation of biotin to ERE was carried out at an ERE to biotin ratio of 20:1 (weight/weight) in 100 mM bicarbonate buffer, pH 8.6, for 1 hr at room temperature. Unreacted biotin was removed using a NAP-5 column equilibrated and eluted with 10 mM Tris, pH 8.0, containing 1 mM EDTA. The biotinylated ERE was stored at 4° C. in presence of 0.1% Kathon as a preservative.

Screening Process: Gel Supershift Assay

Gel supershift assays were performed by a group at the Department of Biochemistry at the University of Wisconsin in Madison, Wis. (USA), to confirm the ELISA data on the selection of the ER antibody capable of binding to the ER activated by ligand (estradiol)/ERE complex.

Enzyme Linked Immunosorbent Assay (ELISA) of ER

To ER-MAb coated microtiter wells were added 50 μl of the assay buffer, 50 μl (5 nmol) estradiol solution, and 100 μl ER positive/negative control, patient cytosol or assay buffer (as the blank). Wells were then incubated for 2 hr at 37° C., followed by x3 wash with wash buffer. To all wells were added 200 μl (250 ng) biotinylated ERE, followed by incubation for another 2 hr at 37° C. Wells were washed for the second time as above, and to each were added 200 μl streptavidin-HRP (1:1000 dilution of the stock solution provided by the manufacturer) and incubated for 1 hr at room temperature. After the last wash as above, 150 μl TMB substrate were added, and the wells were incubated for 10 min, at room temperature. The reaction was stopped by the addition of 150 μl 1M phosphoric acid (stop reagent), and the absorbance was measured at 450 nm using a Vmax [Molecular Devices Corp., Menlo Park, Calif. (USA)] plate reader. A standard curve was constructed by plotting the absorbance values versus the ER concentrations as determined by a ligand binding assay.

Results

The gel supershift assays were performed such that one lane contained ERE alone; a second lane contained ERE and ER-positive cytosol with its ligand; and the remaining six lanes (3–8) contained ERE, ER-positive cytosol with its ligand and different ER MAbs. The ER MAb used for the present studies demonstrated a strong supershift of the activated ER:ERE complex, indicating simultaneous binding of the receptor to both the MAb as well as the ERE.

ERE-biotin conjugates prepared by either selective 5'-phosphorylated end labeling or random labeling showed similar performance. However, the latter provided a simple, rapid, reproducible and more economical procedure, and was, therefore, used for ERE biotinylation.

Figure 3:
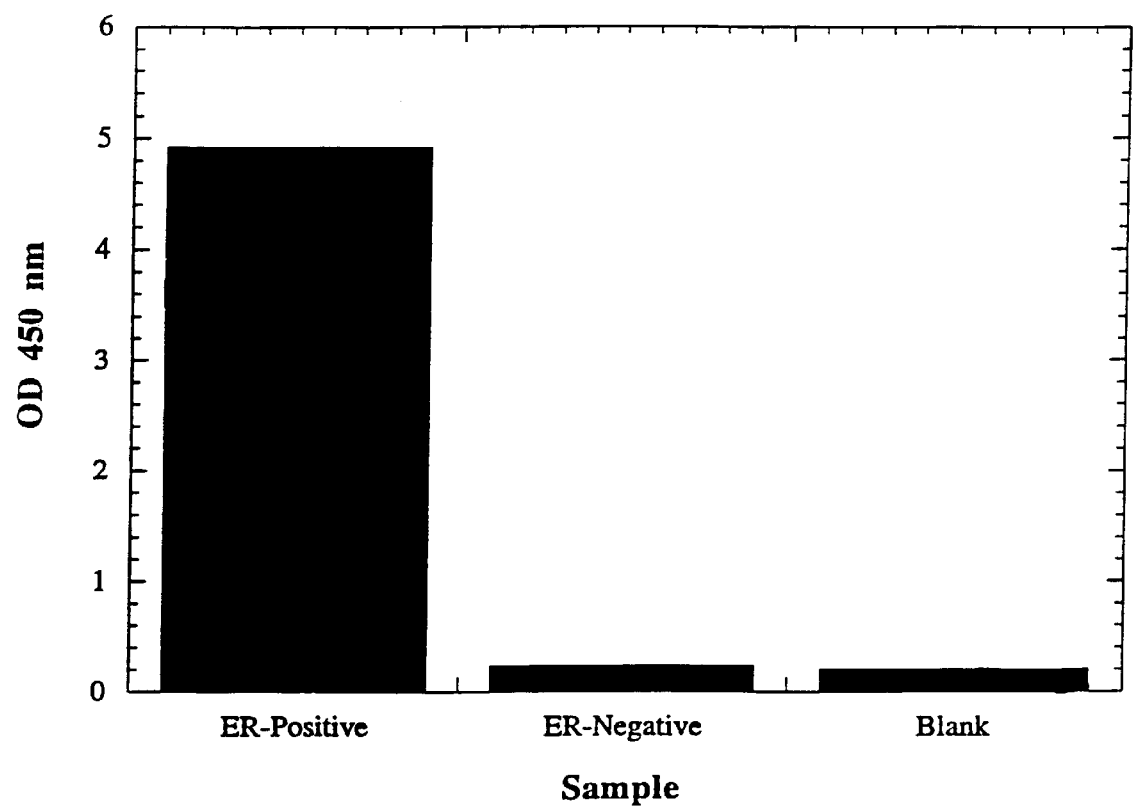
FIGS. 3 and 4 graphically illustrate the results of experiments using the immunoassay format of FIG. 1, wherein functional estrogen receptor (ER) was under assay. ER-positive (+ve) and ER-negative (−ve) controls, and two ER-positive samples of calf uteri were assayed. Those experiments are detailed in Example 1.
Figure 4:
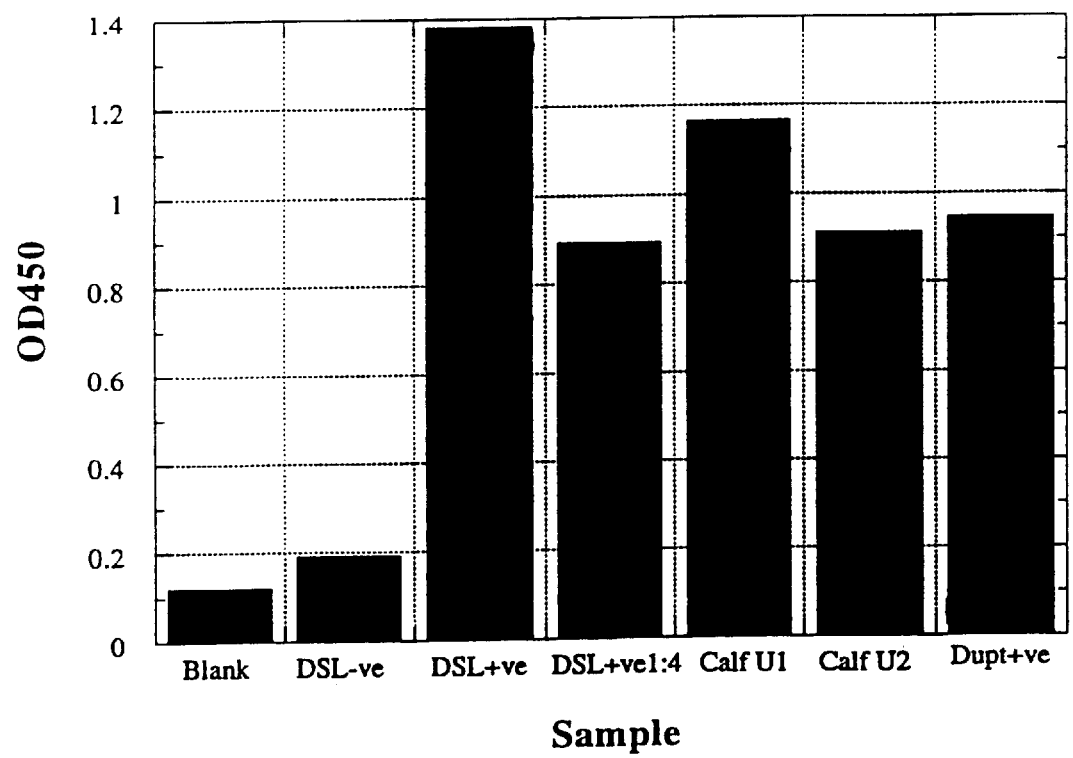

ELISA responses were positive for a number of different ER-positive controls, as well as with two samples of calf uteri which were ER positive by the ligand binding assay. ELISA responses to ER-negative controls were negative. FIGS. 3 and 4 are illustrative of such results. The background represented by blank wells, containing no sample, indicated a negligible contribution of the assay reagents to the actual signals observed.

Figure 5:
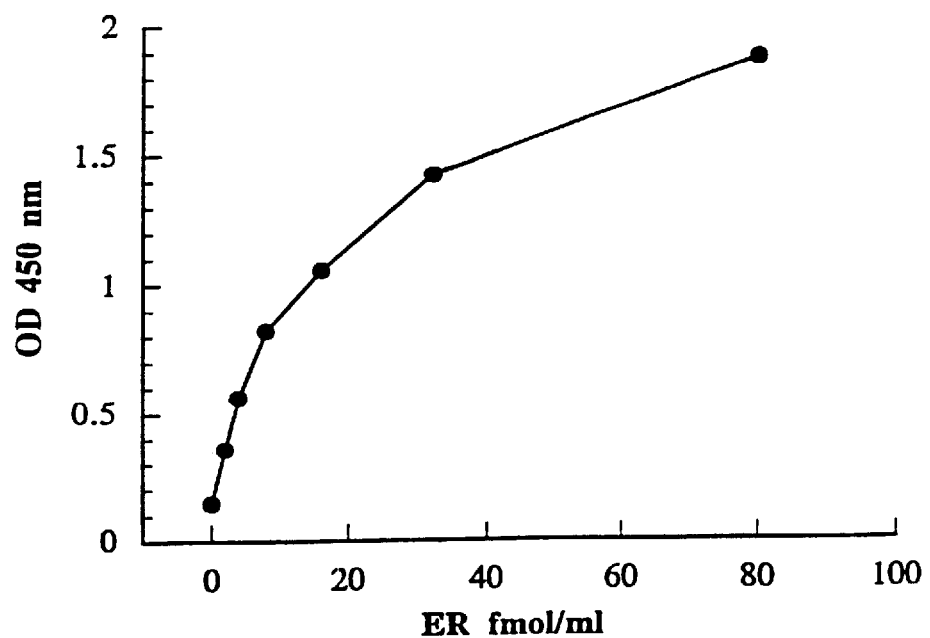
FIG. 5 shows a representative standard curve for the immunoassay in the format of FIG. 1 wherein functional ER is under assay.

FIG. 5 shows a representative standard curve for ER produced by the newly developed MAb:ERE assay of this invention.

Figure 6:
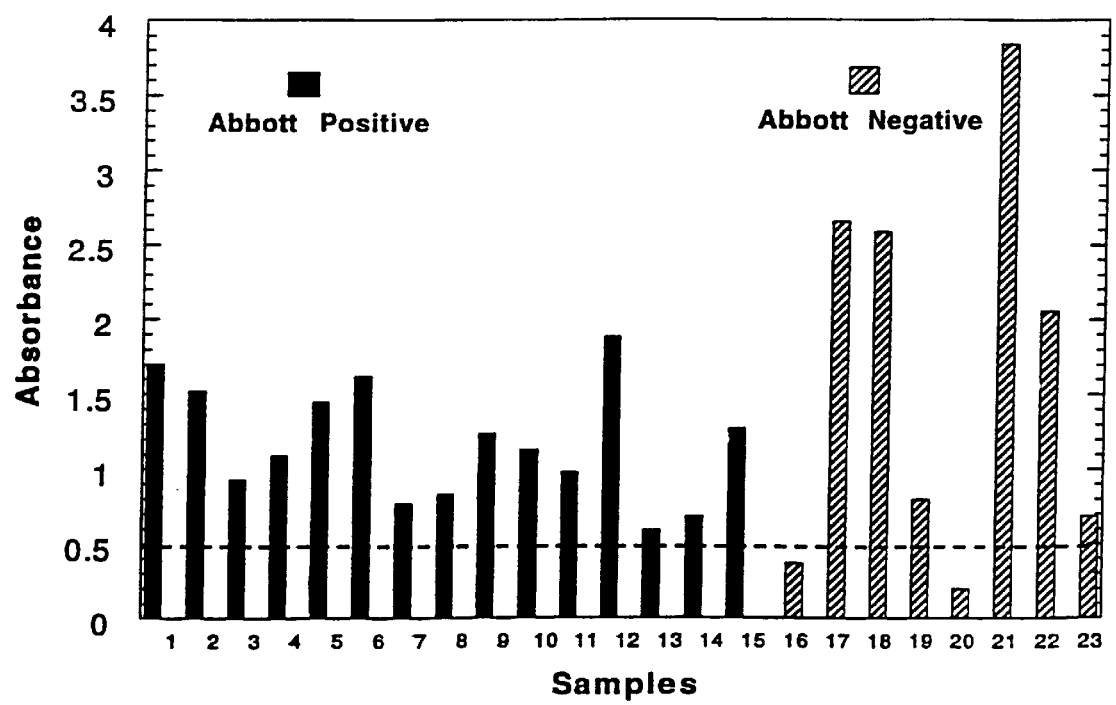
FIG. 6 graphically illustrates results using the immunoassay format of FIG. 1 wherein functional ER in breast cancer cytosols was assayed.

Data obtained with clinical samples is shown in FIG. 6. A total of 23 breast cancer cytosols previously assayed by the Abbott ER EIA were tested by the MAb:ERE assay. using an arbitrary cut-off of 0.5 absorbance unit, all Abbott ER-positive samples were also found positive by the present assay, however, a few were relatively low and just above the arbitrary cut-off. Few of the Abbott ER-negative samples were also found positive by the MAb:ERE assay.

The descriptions of the foregoing embodiments of the invention have been presented for purposes of illustration and description. They are not intended to be exhaustive or to limit the invention to the precise form disclosed, and obviously many modifications and variations are possible in light of the above teachings. The embodiments were chosen and described in order to best explain the principles of the invention and its practical application to enable thereby others skilled in the art to best utilize the invention in various embodiments and with various modifications as are suited to the particular use contemplated. It is intended that the scope of the invention be defined by the claims appended hereto.

All references cited herein are hereby incorporated by reference.

I claim:

1. A method of detecting the presence or absence of functional nuclear receptors in a cell or tissue sample, or of detecting and quantitating functional nuclear receptors in a cell or tissue sample comprising:

(a) contacting said sample with the following: (1) ligand to which the nuclear receptor under assay binds; (2) antibody that is capable of specifically binding to the nuclear receptor under assay when said receptor is bound both to its associated ligand and response element; and (3) a nucleic acid reagent containing one or more response element segments to which the nuclear receptor under assay binds; wherein either said antibody or said nucleic acid reagent is attached to a solid phase, and wherein the sample may be contacted with the ligand, the nucleic acid reagent and the antibody components simultaneously, with two of said components simultaneously, or sequentially with said three components in any order; and (b) correlating the specific binding of said nucleic acid reagent, said ligand and said antibody to a substance in said sample with the presence of functional nuclear receptors in said sample, or correlating the amount of complexes formed by the specific binding of said nucleic acid reagent, said ligand, said antibody and a substance in said sample with the amount of functional nuclear receptors in said sample.

2. The method according to claim 1 wherein the steps are carried out in an automated immunoassay system.

3. The method according to claim 1 wherein said antibody is attached to the solid phase, and wherein said nucleic acid reagent is directly or indirectly linked to a detectable marker; or wherein said nucleic acid reagent is attached to the solid phase, and wherein said antibody is directly or indirectly linked to a detectable marker.

4. The method according to claim 3 wherein said antibody is attached to the solid phase; wherein the antibody and ligand are incubated with said sample, and thereafter uncomplexed sample components are removed, before the nucleic acid reagent is added; and wherein said nucleic acid reagent is directly or indirectly linked to a detectable marker.

5. The method according to claim 3 wherein the nucleic acid reagent is attached to the solid phase and is in excess; wherein non-specific binding of proteins, other than the nuclear receptor under assay, in the sample to the nucleic acid reagent is prevented by including appropriate non-specific nucleic acids; wherein the nucleic acid reagent and the ligand are incubated with said sample, and thereafter, sample components uncomplexed to the solid phase are removed, before the antibody is added; and wherein said antibody is directly or indirectly bound to a detectable marker.

6. The method according to claim 1 wherein the nuclear receptor under assay is a steroid/thyroid hormone receptor selected from the group consisting of steroid hormone receptors, receptors for hormonal forms of vitamin A and D, thyroid hormones, and retinoic acid receptors.

7. The method according to claim 1 wherein the nuclear receptor under assay is selected from the group consisting of steroid hormone receptors.

8. The method according to claim 7 wherein the steroid hormone receptor is selected from the group consisting of estrogen receptor, progesterone receptor, glucocorticoid receptor, mineralocorticoid receptor, androgen receptor, and vitamin D3 receptor.

9. The method according to claim 7 wherein the steroid hormone receptor is selected from the group consisting of estrogen receptor and progesterone receptor.

10. The method according to claim 7 wherein the steroid hormone receptor is an estrogen receptor.

11. The method according to claim 1 wherein said cell or tissue sample is a cell or tissue extract, or a cell lysate.

12. The method according to claim 1 wherein said cell or tissue sample is a cytosol and/or a nuclear extract.

13. The method according to claim 1 wherein said cell or tissue sample is vertebrate.

14. The method according to claim 1 wherein said cell or tissue sample is mammalian.

15. The method according to claim 1 wherein said cell or tissue sample is human.

16. The method according to claim 3 wherein said detectable marker is selected from the group consisting of radionuclides, fluorescers, bioluminescers, chemiluminescers, dyes, enzymes, coenzymes, enzyme substrates, enzyme cofactors, enzyme inhibitors, enzyme subunits, metal ions, and free radicals.

17. The method according to claim 16 wherein the detectable marker is either selected from the group consisting of acridinium esters, acridinium sulfonyl carboxamides, fluorescein, luminol, umbelliferone, isoluminol derivatives, photoproteins, and luciferases, or is produced by an enzymatic reaction upon a substrate.

18. The method according to claim 3 wherein the detectable marker is either an acridinium ester or is produced by an enzymatic reaction with a chemiluminescent substrate and an enzyme selected from the group consisting of alkaline phosphatase, glucose oxidase, glucose 6-phosphate dehydrogenase, $\alpha$-, $\beta$-galactosidase, horseradish peroxidase, and xanthine oxidase.

19. The method according to claim 18 wherein the enzyme is alkaline phosphatase, and its substrate is an adamantyl 1,2-dioxetane aryl phosphate with or without an enhancer molecule; or wherein the enzyme is horseradish peroxidase, and its substrate is 2', 3', 6'-trifluorophenyl 3-methoxy-10-methylacridan-9-carboxylate.

20. The method according to claim 19 wherein the enzyme is alkaline phosphatase, and its substrate is a disodium salt of 4-methoxy-4-(3-phosphatephenyl) spiro [1,2-dioxetane-3,2'-adamantane] with or without 1-(trioctylphosphonium methyl)-4-(tributylphosphonium methyl) benzene dichloride as an enhancer.

21. The method according to claim 4 wherein said nucleic acid reagent is conjugated to a member of a binding pair, and the detectable marker is conjugated to the other member of said binding pair; wherein said nucleic acid reagent is incubated with the solid phase complex, and thereafter, uncomplexed reagents are removed, before the conjugated detectable marker is added and then detected, or detected and quantitated.

22. The method according to claim 21 wherein said binding pair comprises biotin and either avidin or streptavidin.

23. The method according to claim 22 wherein the nucleic acid reagent is biotinylated, and the avidin or streptavidin is conjugated to alkaline phosphatase or horseradish peroxidase.

24. The method according to claim 23 wherein the nucleic acid reagent is biotinylated either selectively or randomly at multiple sites.

25. The method according to claim 24 wherein the nucleic acid reagent is biotinylated selectively at the 5'phosphorylated ends and/or at multiple sites that are not within a response element core sequence.

26. The method according to claim 3 wherein the sample tested is from a biopsied tissue or from a cell suspension from a breast cancer patient, and the nuclear receptor under assay is a steroid hormone receptor.

27. The method according to claim 26 wherein the sample is from a fine needle aspirate or from a stereotactic needle biopsy.

28. The method according to claim 1 wherein the one or more response element segments to which the nuclear receptor under assay binds contain a sequence selected from the group consisting of: SEQ. ID. NOS.: 1–3 and 5–14.

29. The method according to claim 1 wherein said nucleic acid reagent is double-stranded and contains two to eight response element segments, wherein each of the response element core sequences consists of two inverted repeats, which are the same in each segment, and wherein the central spacer of three base pairs separating the inverted repeats may vary between or among the segments; and wherein the sequences flanking the core sequences of said response element segments are AT-rich, and may vary in sequence between or among the response element segments.

30. The method according to claim 1 wherein said nucleic acid reagent contains one to fifteen copies of a response element segment.

31. The method according to claim 9 wherein the steroid hormone receptor under assay is an estrogen receptor, and wherein the estrogen response element segment has as its sequence or contains a sequence selected from the group consisting of SEQ. ID. NOS. 3, 7–10 and 12–14.

32. The method according to claim 31 wherein the nucleic acid reagent has SEQ. ID. NO.: 1 as its sequence, or is a monomer, dimer, trimer or tetramer of SEQ. ID. NO. 7.

33. The method according to claim 1 wherein the nucleic acid reagent is DNA that is isolated from naturally occurring sources.

34. The method according to claim 1 wherein the nucleic acid reagent is prepared recombinantly or synthetically.

35. The method according to claim 34 wherein the nuclear receptor under assay is an estrogen receptor; wherein the nucleic acid reagent contains more than one copy of an estrogen response element segment; and wherein the nucleic acid reagent is prepared synthetically and selectively biotinylated at the 5' phosphorylated ends and/or at sites not within any core sequences of said estrogen response element segments.

36. The method according to claim 34 wherein the nucleic acid reagent contains a monomer, dimer, trimer, tetramer, pentamer, septamer or octamer of an estrogen response element segment; and wherein the nucleic acid reagent is selectively biotinylated at the 5' phosphorylated ends and/or at multiple sites that are not within the core sequences of the estrogen response elements.

37. The method according to claim 36 wherein the core sequence is contained in a sequence selected from the group consisting of SEQ. ID. NOS.: 7–10 and 12–14.

38. The method according to claim 1 wherein the nucleic acid reagent further comprises one or two oligonucleotide segments that are single-stranded at either or both ends of said nucleic acid reagent, and wherein said oligonucleotide segment(s) is or are complementary to a labeled oligomer probe.

39. The method according to claim 1 wherein said solid phase is particulate.

40. The method according to claim 39 wherein said particulate solid phase comprises magnetic or paramagnetic particles.

41. The method according to claim 1 wherein said solid phase is a solid wall surface of a container or the surface of beads.

42. The method of claim 41 wherein said solid phase is a microtiter plate well.

43. The method according to claim 1 wherein said sample is from a biopsied tissue or from a cell suspension from a patient who has cancer or is suspected of having cancer.

44. The method according to claim 43 wherein the sample is from a fine needle aspirate or from a stereotactic needle biopsy.

45. The method according to claim 43 wherein said cancer is selected from the group consisting of breast, endometrial, uterine, cervical, ovarian, prostrate, vaginal or vulval cancers.

46. The method according to claim 45 wherein the steroid hormone receptor under assay is estrogen receptor, and said cancer is breast cancer.

47. The method according to claim 43 wherein the amount of biopsied tissue necessary for preparing the sample to be assayed is less than 50 mg.

48. The method according to claim 47 wherein the amount of biopsied tissue required is between 10 mg and 25 mg.

49. The method according to claim 1 wherein the antibody is a monoclonal antibody.

50. The method according to claim 1 wherein the antibody is a biologically active antibody fragment.

51. The method according to claim 4 wherein a signal amplification system is used to amplify the signal from the detectable marker.

52. The method according to claim 51 wherein said signal amplification system comprises using a nucleic acid reagent that is biotinylated at multiple sites; after removing uncomplexed components, adding streptavidin/avidin conjugated to horseradish peroxidase or alkaline phosphatase; and then after removing uncomplexed components, adding an appropriate chemiluminescent substrate.

53. The method according to claim 51 comprising the use of nucleic acid multimers that each comprise (i) an oligonucleotide unit that is complementary to a segment of the nucleic acid reagent, and (ii) a multiplicity of second oligonucleotide units that are complementary to an oligonucleotide that is labeled directly or indirectly.

54. The method according to claim 1 wherein said antibody is attached to the solid phase, and wherein complexes of said antibody, said ligand, said functional nuclear receptor, and said nucleic acid reagent are detected, or are detected and quantitated by the use of a signal amplification system, comprising:

(a') contacting said complexes under hybridizing conditions with a nucleic acid multimer, said multimer comprising (i) at least one oligonucleotide unit that is complementary to a segment of the nucleic acid reagent and (ii) a multiplicity of second oligonucleotide units that are complementary to an oligonucleotide that is labeled either directly or indirectly;

(b') removing unbound multimer;

(c') contacting under hybridizing conditions the solid phase complex product of step (a') with the labeled oligonucleotide;

(d') removing unbound labeled oligonucleotides; and (e') detecting signal from any label on the solid phase complex product of step (d') and correlating that signal with the presence of nuclear receptors under assay that are functional, or detecting and quantitating the amount of signal from label on the solid phase complex product of step (d') and correlating the amount of signal with the amount of nuclear receptors under assay that are functional.

55. The method according to claim 54 wherein the label is selected from the group consisting of radionuclides, fluorescers, bioluminescers, chemiluminescers, dyes, enzymes, coenzymes, enzyme substrates, enzyme cofactors, enzyme inhibitors, enzyme subunits, metal ions, free radicals and particles.

56. The method according to claim 55 wherein the label is either an acridinium ester or is produced by an enzymatic reaction with an enzyme selected from the group consisting of alkaline phosphatase, glucose oxidase, glucose 6-phosphate dehydrogenase, $\alpha$-, $\beta$-galactosidase, horseradish peroxidase, and xanthine oxidase.

57. The method according to claim 56 wherein the enzyme is alkaline phosphatase, and its substrate is an adamantyl 1,2-dioxetane aryl phosphate with or without an enhancer molecule, or is paranitrophenyl phosphate; or wherein the enzyme is horseradish peroxidase, and its substrate is either tetramethyl benzidine, or 2', 3', 6'-trifluorophenyl 3-methoxy-10-methylacridan-9 carboxylate.

58. The method according to claim 57 wherein the enzyme is alkaline phosphatase, and its substrate is a disodium salt of 4-methoxy-4-(3-phosphatephenyl)spiro [1,2-dioxetane-3,2'-adamantane] with or without 1-(trioctylphosphonium methyl)-4-(tributylphosphonium methyl) benzene dichloride as an enhancer.

59. The method according to claim 54 wherein the sample is prepared from biopsied tissue from a patient having cancer or suspected of having cancer, wherein the amount of biopsied tissue necessary for preparing said sample is 25 mg or less.

60. A method of developing a prognosis and/or a treatment program for a cancer patient comprising:

(a) performing the method of claim 1 wherein said sample is prepared from biopsied tissue or from a cell suspension from said patient, and determining either that functional nuclear receptors are present or absent in said sample, or that functional nuclear receptors are present and the quantity of said functional nuclear receptors in said sample; and (b) making a prognosis for said patient and/or a decision on whether endocrine therapy would be useful in a treatment program for said patient based on the results from step (a).

61. The method according to claim 60 wherein said cancer patient has cancer of the breast, endometrium, uterus, cervix, ovaries, prostate, vagina or vulva.

62. The method according to claim 60 wherein the nuclear receptor under assay is human estrogen receptor; wherein the patient is a breast cancer patient; and wherein the presence of functional estrogen receptors detected, or detected and quantitated in said sample, indicates a positive prognosis, and that endocrine therapy would be helpful in a treatment program for said patient.

63. The method according to claim 62 wherein said endocrine therapy is selected from the group consisting of administration of anti-estrogen compounds, performance of an ovariectomy, performance of a hypophysectomy, and the administration of androgen.

64. A test kit for performing the method of claim 1 comprising:

(a) an antibody that is capable of specifically binding to the nuclear receptor under assay when said receptor is bound both to its associated ligand and response element;

(b) ligand to the nuclear receptor under assay; and (c) a nucleic acid reagent containing one or more response element segments to which the nuclear receptor under assay binds;

wherein either said antibody or said nucleic acid reagent is attached to a solid phase.

* * * * *

UNITED STATES PATENT AND TRADEMARK OFFICE
CERTIFICATE OF CORRECTION

PATENT NO. : 5,770,176

DATED : June 23, 1998

INVENTOR(S) : Ruhangiz Dokhi Nargessi

It is certified that error appears in the above-identified patent and that said Letters Patent is hereby corrected as shown below:

Column 11, line 30, "37°C." should read -- 37°C, --;

Column 17, lines 44-45, "Nterminal region" should read
 -- N-terminal region --;

Column 23, lines 41-42, "about 20°C. to 80°C., more usually
 from about 35°C. to 70°C., particularly 35°C."
 should read -- about 20°C to 80°C, more usually
 from about 35°C to 70°C, particularly 35°C --;

Column 24, line 46, "Portland, (USA)" should read
 -- Portland, OR (USA) --;

Column 25, line 5, "40°C." should read -- 4°C.,--.

Column 27 in the Sequence Listing under SEQ ID NO: 2(x)(A)
 "AUTHORS: Beato, M." should read -- AUTHOR:
 Beato, M. --;

Column 27 in the Sequence Listing under SEQ ID NO: 3(x)(A)
 "AUTHORS: Beato, M." should read -- AUTHOR:
 Beato, M. --;

Column 29 in the Sequence Listing under SEQ ID NO: 4(x)(A)
 "AUTHORS: Beato, M." should read -- AUTHOR:
 Beato, M. --;

Column 29 in the Sequence Listing under SEQ ID NO: 5(x)(A)
 "AUTHORS: Beato, M." should read -- AUTHOR:
 Beato, M. --;

Column 31 in the Sequence Listing under SEQ ID NO: 6(x)(A)
 "AUTHORS: Beato, M." should read -- AUTHOR:
 Beato, M. --.

UNITED STATES PATENT AND TRADEMARK OFFICE
CERTIFICATE OF CORRECTION

PATENT NO. : 5,770,176
DATED : June 23, 1998
INVENTOR(S) : Ruhangiz Dokhi Nargessi It is certified that error appears in the above-identified patent and that said Letters Patent is hereby corrected as shown below:

Column 14, Table 1, line 53, "GGTCACAGTGACC" should read -- GGTCACAGTGACC --;
Column 19, line 66, "$^{131}$;" should read -- $^{131}I$; --;
Column 20, line 2, "calorimetric" should read -- colorimetric --;
Column 26, line 35, "using" should read -- Using --.
Column 31, in the Sequence Listing under "(2) INFORMATION FOR SEQ ID NO: 10, (ii) MOLECULAR TYPE:", "(A) DESCRIPTION: an estrogen response element (ERE) segment" should read -- (A) DESCRIPTION: an estrogen response element (ERE) segment consensus sequence --.

Signed and Sealed this

Twentieth Day of June, 2000

Attest:

Attesting Officer

Q. TODD DICKINSON
Director of Patents and Trademarks